United States Patent
Trucksis

(10) Patent No.: US 7,582,424 B2
(45) Date of Patent: Sep. 1, 2009

(54) ACCESSORY CHOLERA ENTEROTOXIN AND ANALOGS THEREOF AS ACTIVATORS OF CALCIUM DEPENDENT CHLORIDE CHANNEL

(75) Inventor: Michele Trucksis, Wayland, MA (US)

(73) Assignee: University of Maryland, Baltimore, Baltimore, MD (US)

( * ) Notice: Subject to any disclaimer, the term of this patent is extended or adjusted under 35 U.S.C. 154(b) by 1171 days.

(21) Appl. No.: 10/333,610

(22) PCT Filed: Jul. 27, 2001

(86) PCT No.: PCT/US01/23530

§ 371 (c)(1), (2), (4) Date: Jun. 10, 2003

(87) PCT Pub. No.: WO02/09642

PCT Pub. Date: Feb. 7, 2002

(65) Prior Publication Data

US 2004/0110672 A1    Jun. 10, 2004

Related U.S. Application Data

(60) Provisional application No. 60/222,110, filed on Jul. 28, 2000.

(51) Int. Cl.
*C12Q 1/68* (2006.01)
*A61K 38/00* (2006.01)
*A01N 37/00* (2006.01)

(52) U.S. Cl. .............................. 435/6; 514/557; 514/12

(58) Field of Classification Search ...................... 435/6; 514/557, 12
See application file for complete search history.

(56) References Cited

U.S. PATENT DOCUMENTS

| | | | |
|---|---|---|---|
| 4,328,209 A | | 5/1982 | Finkelstein et al. |
| 5,470,729 A | * | 11/1995 | Kaper et al. .................. 435/6 |
| 5,602,110 A | | 2/1997 | Drumm et al. |
| 5,658,776 A | | 8/1997 | Flotte et al. |
| 5,674,898 A | * | 10/1997 | Cheng et al. ................ 514/557 |
| 5,750,571 A | | 5/1998 | Cheng et al. |
| 6,077,826 A | * | 6/2000 | Tomich et al. ................ 514/12 |

FOREIGN PATENT DOCUMENTS

| | | |
|---|---|---|
| CH | 645 270 | 9/1984 |
| WO | WO 9739766 | * 10/1997 |

OTHER PUBLICATIONS

Trucksis et al. "Accessory cholera enterotoxin (Ace), the third toxin of a *Vibrio cholerae* virulence cassette" Proc. Natl. Acad. Sci. U.S.A. 90 (11), 5267-5271, 1993.*
GenBank acc# Z22569.*
Trucksis, et al. "Accessory cholera enterotoxin (Ace), the third toxin of a *Vibrio cholerae* virulence cassette" Proc. Natl. Acad. Sci. U.S.A. 90 (11), 5267-5271 (1993).*
GenBank entry under accession # Z22569.*
SEQ ID No. 5 alingment ( see result 4 AAR86556), Nov. 7, 2008.*

* cited by examiner

*Primary Examiner*—Robert Mondesi
*Assistant Examiner*—Khatol Shahnan-Shah
(74) *Attorney, Agent, or Firm*—Sughrue Mion, PLLC

(57) ABSTRACT

*Vibrio cholerae* accessory cholera enterotoxin (ACE) activates a calcium dependent chloride channel. Ace and Ace analogs can be administered to patients to treat diseases involving defects in chloride secretion by the cystitis fibrosis transmembrane receptor (CFTR). Cystic fibrosis, Dent's disease, X-linked nephrolithiasis, X-linked recessive hypophosphatemic rickets, autosomal dominant myotonia congenita and autosomal recessive general myotonia can be treated by the administration of Ace or an Ace analog. For cystic fibrosis, administration of Ace or an Ace analog increases chloride secretion in the lungs which increases the amount of airway surface water in the lumen of the lungs.

9 Claims, 42 Drawing Sheets

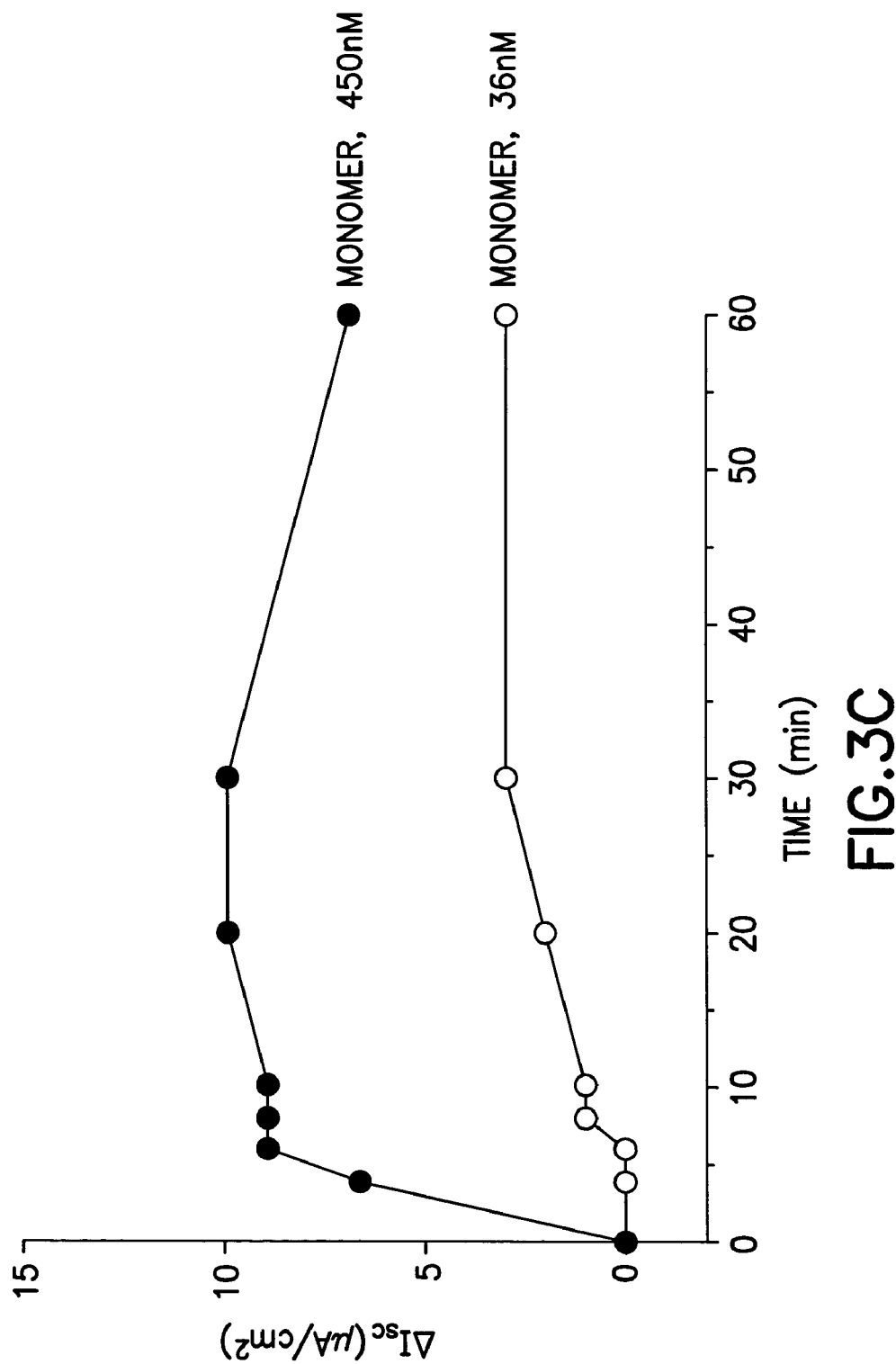

```
  1  atgcttatga  tggacaccct  ttatgactgg  ctaattgatg  gcttacgtg   gcttgtgatc
 61  aagctcggta  ttatgtggat  tgagagcaag  attttttgtta tccaattctt  ctgggagatg
121  tcccagaaag  tgattgatat  gttaccatc   tatcgctta   tccaacaggc  tatcgatatg
181  ctgcctcctc  aatacagcgg  ctttctgttc  tttttagggt  tagaccaagc  gctggctatc
241  gtgcttcagg  ctttgatgac  ccgttttgcc  ctgcgagcgt  taaacctatg  a
```

SEQ ID NO: 1

FIG. 16

```
Met Leu Met Met Asp Thr Leu Tyr Asp Trp Leu Ile Asp Gly Phe Thr
 1               5                  10                  15
Trp Leu Val Ile Lys Leu Gly Ile Met Trp Ile Glu Ser Lys Ile Phe
                20                  25                  30
Val Ile Gln Phe Phe Trp Glu Met Ser Gln Lys Val Ile Asp Met Phe
                35                  40                  45
Thr Ile Tyr Pro Leu Ile Gln Gln Ala Ile Asp Met Leu Pro Pro Gln
                50                  55                  60
Tyr Ser Gly Phe Phe Leu Phe Leu Gly Leu Asp Gln Ala Leu Ala Ile
 65                 70                  75                  80
Val Leu Gln Ala Leu Met Thr Arg Phe Ala Leu Arg Ala Leu Asn Leu
                85                  90                  95
```

SEQ ID NO: 2

FIG. 17

Met Leu Met Met Asp Thr Leu Tyr Asp Trp Leu Ile Asp Gly Phe Thr
1               5                   10                  15
Trp Leu Val Ile Lys Leu Gly Ile Met Trp Ile Glu Ser Lys Ile Phe
            20                  25                  30
Val Ile Gln Phe Phe Trp Glu Met Ser Gln Lys Val Ile Asp Met Phe
            35                  40                  45
Thr Ile Tyr Pro Leu Ile Gln Gln Ala Ile Asp Met Leu Pro Pro Gln
        50                  55                  60
Tyr Ser Gly Phe Leu Phe Phe Leu Gly
65                  70

SEQ ID NO: 3

FIG.18

Met Leu Met Met Asp Thr Leu Tyr Asp Trp Leu Ile Asp Gly Phe Thr
1               5                   10                  15

Trp Leu Val Ile Lys Leu Gly Ile Met Trp Ile Glu Ser Lys Ile Phe
                20                  25                  30

Val Ile Gln Phe Phe Trp Glu Met Ser Gln Lys Val Ile Asp Met Phe
                35                  40                  45

Thr Ile Tyr Pro Leu Ile Gln Gln Ala
                50              55

SEQ ID NO: 4

FIG. 19

Met Leu Met Met Asp Thr Leu Tyr Asp Trp Leu Ile Asp Gly Phe Thr
1               5                   10                  15
Trp Leu Val Ile Lys Leu Gly Ile Met Trp Ile Glu Ser Lys Ile Phe
            20                  25                  30
Val Ile Gln Phe Phe Trp Glu Met Ser Gln
            35                  40

SEQ ID NO: 5

FIG.20

Met Leu Met Met Asp Thr Leu Tyr Asp Trp Leu Ile Asp Gly Phe Thr
1               5                   10                  15
Trp Leu Val Ile Lys Leu Gly Ile Met Trp Ile Glu Ser Lys Ile Phe
            20                  25                  30
Val Ile

SEQ ID NO: 6

FIG.21

```
Met Leu Met Met Asp Thr Leu Tyr Asp Trp Leu Ile Asp Gly Phe Thr
1               5                   10                  15
Trp Leu Val Ile Lys Leu Gly Ile Met Trp Ile Glu Ser Lys Ile Phe
            20                  25                  30
Val Ile Gln Phe Trp Glu Met Ser Gln Ala Val Ile Asp Met Phe
        35                  40                  45
Thr Ile Tyr Pro Leu Ile Gln Ala Ile Asp Met Leu Pro Pro Gln
    50                  55                  60
Tyr Ser Gly Phe Leu Phe Leu Gly Leu Asp Gln Ala Leu Ala Ile
65              70                  75                  80
Val Leu Gln Ala Leu Met Thr Arg Phe Ala Leu Arg Ala Leu Asn Leu
            85                  90                  95
```

SEQ ID NO:7

FIG.22

Met Leu Met Met Asp Thr Leu Tyr Asp Trp Leu Ile Asp Gly Phe Thr
1               5                   10                  15

Trp Leu Val Ile Ala Leu Gly Ile Met Trp Ile Glu Ser Lys Ile Phe
        20                  25                  30

Val Ile Gln Phe Phe Trp Glu Met Ser Gln Lys Val Ile Asp Met Phe
            35                  40                  45

Thr Ile Tyr Pro Leu Ile Gln Gln Ala Ile Asp Met Leu Pro Pro Gln
50                  55                  60

Tyr Ser Gly Phe Phe Leu Gly Leu Asp Gln Ala Leu Ala Ile
65                  70                  75                  80

Val Leu Gln Ala Leu Met Thr Arg Phe Ala Leu Arg Ala Leu Asn Leu
        85                  90                  95

FIG.23

SEQ ID NO: 8

Met Leu Met Met Asp Thr Leu Tyr Asp Trp Leu Ile Asp Gly Phe Thr
1               5                   10                  15

Trp Leu Val Ile Lys Leu Gly Ile Met Trp Ile Glu Ser Ala Ile Phe
            20                  25                  30

Val Ile Gln Phe Phe Trp Glu Met Ser Gln Lys Val Ile Asp Met Phe
        35                  40                  45

Thr Ile Tyr Pro Leu Ile Gln Gln Ala Ile Asp Met Leu Pro Pro Gln
50                  55                  60

Tyr Ser Gly Phe Leu Phe Phe Leu Gly Leu Asp Gln Ala Leu Ala Ile
65                  70                  75                  80

Val Leu Gln Ala Leu Met Thr Arg Phe Ala Leu Arg Ala Leu Asn Leu
            85                  90                  95

SEQ ID NO: 9

FIG.24

```
Met Leu Met Met Asp Thr Leu Tyr Asp Trp Leu Ile Asp Gly Phe Thr
 1               5                  10                  15
Trp Leu Val Ile Lys Leu Gly Ile Met Trp Ile Ala Ser Lys Ile Phe
            20                  25                  30
Val Ile Gln Phe Phe Trp Glu Met Ser Gln Lys Val Ile Asp Met Phe
        35                  40                  45
Thr Ile Tyr Pro Leu Ile Gln Gln Ala Ile Asp Met Leu Pro Pro Gln
50                  55                  60
Tyr Ser Gly Phe Leu Phe Phe Leu Gly Leu Asp Gln Ala Leu Ala Ile
65                  70                  75                  80
Val Leu Gln Ala Leu Met Thr Arg Phe Ala Leu Arg Ala Leu Asn Leu
            85                  90                  95
```

SEQ ID NO: 10

FIG. 25

Met Leu Met Met Asp Thr Leu Tyr Asp Trp Leu Ile Asp Gly Phe Thr
1               5                   10                  15

Trp Leu Val Ile Lys Leu Gly Ile Met Trp Ile Glu Ser Lys Ile Phe
            20                  25                  30

Val Ile Gln Phe Phe Trp Ala Met Ser Gln Lys Val Ile Asp Met Phe
            35                  40                  45

Thr Ile Tyr Pro Leu Ile Gln Gln Ala Ile Asp Met Leu Pro Pro Gln
            50                  55                  60

Tyr Ser Gly Phe Leu Phe Phe Leu Gly Leu Asp Gln Ala Leu Ala Ile
65              70                  75                  80

Val Leu Gln Ala Leu Met Thr Arg Phe Ala Leu Arg Ala Leu Asn Leu
            85                  90                  95

SEQ ID NO: 11

FIG. 26

Ala Leu Met Met Asp Thr Leu Tyr Asp Trp Leu Ile Asp Gly Phe Thr
1               5                   10                  15

Trp Leu Val Ile Lys Leu Gly Ile Met Trp Ile Glu Ser Lys Ile Phe
        20                  25                  30

Val Ile Gln Phe Phe Trp Glu Met Ser Gln Lys Val Ile Asp Met Phe
        35                  40                  45

Thr Ile Tyr Pro Leu Ile Gln Gln Ala Ile Asp Met Leu Pro Pro Gln
        50                  55                  60

Tyr Ser Gly Phe Leu Phe Phe Leu Gly Leu Asp Gln Ala Leu Ala Ile
65              70                  75                  80

Val Leu Gln Ala Leu Met Thr Arg Phe Ala Leu Arg Ala Leu Asn Leu
        85                  90                  95

SEQ ID NO: 12

FIG.27

```
Met Leu Ala Met Asp Thr Leu Tyr Asp Trp Leu Ile Asp Gly Phe Thr
1               5                   10                  15
Trp Leu Val Ile Lys Leu Gly Ile Met Trp Ile Glu Ser Lys Ile Phe
                20                  25                  30
Val Ile Gln Phe Phe Trp Glu Met Ser Gln Lys Val Ile Asp Met Phe
                35                  40                  45
Thr Ile Tyr Pro Leu Ile Gln Gln Ala Ile Asp Met Leu Pro Pro Gln
50                  55                  60
Tyr Ser Gly Phe Leu Phe Phe Leu Gly Leu Asp Gln Ala Leu Ala Ile
65                  70                  75                  80
Val Leu Gln Ala Leu Met Thr Arg Phe Ala Leu Arg Ala Leu Asn Leu
                85                  90                  95
```

SEQ ID NO:13    FIG.28

Met Leu Met Ala Asp Thr Leu Tyr Asp Trp Leu Ile Asp Gly Phe Thr
1               5                   10                  15

Trp Leu Val Ile Lys Leu Gly Ile Met Trp Ile Glu Ser Lys Ile Phe
                20                  25                  30

Val Ile Gln Phe Phe Trp Glu Met Ser Gln Lys Val Ile Asp Met Phe
                35                  40                  45

Thr Ile Tyr Pro Leu Ile Gln Ala Ile Asp Met Leu Pro Pro Gln
50                  55                  60

Tyr Ser Gly Phe Leu Phe Phe Leu Gly Leu Asp Gln Ala Leu Ala Ile
65                  70                  75                  80

Val Leu Gln Ala Leu Met Thr Arg Phe Ala Leu Arg Ala Leu Asn Leu
                85                  90                  95

SEQ ID NO: 14

FIG.29

Met Leu Met Met Asp Thr Leu Tyr Asp Trp Leu Ile Asp Gly Phe Thr
1               5                   10                  15

Trp Leu Val Ile Lys Leu Gly Ile Met Trp Ile Glu Ser Lys Ile Phe
            20                  25                  30

Val Ile Gln Phe Phe Trp Glu Met Asp Met Phe Thr Ile Tyr Pro Leu
            35                  40                  45

Ile Gln Gln Ala Ile Asp Met Leu Pro Pro Gln Tyr Ser Gly Phe Leu
        50                  55                  60

Phe Phe Leu Gly Leu Asp Gln Ala Leu Ala Ile Val Leu Gln Ala Leu
65                  70                  75                  80

Met Thr Arg Phe Ala Leu Arg Ala Leu Asn Leu
            85                  90

SEQ ID NO: 15

FIG. 30

```
Met Leu Met Met Asp Thr Leu Tyr Asp Trp Leu Ile Asp Gly Phe
 1               5                  10                  15
Trp Leu Val Ile Lys Leu Gly Ile Met Trp Ile Glu Ser Lys Ile Phe
            20                  25                  30
Val Ile Asp Met Phe Thr Ile Tyr Pro Leu Ile Gln Gln Ala Ile Asp
            35                  40                  45
Met Leu Pro Pro Gln Tyr Ser Gly Phe Phe Leu Phe Leu Gly Leu Asp
 50                  55                  60
Gln Ala Leu Ala Ile Val Leu Gln Ala Leu Met Thr Arg Phe Ala Leu
 65                  70                  75                  80
Arg Ala Leu Asn Leu
             85
```

FIG.31

SEQ ID NO: 16

Met Leu Met Met Asp Thr Leu Tyr Asp Trp Leu Ile Asp Gly Phe Thr
1               5                   10                  15
Trp Leu Val Ile Ala Leu Gly Ile Met Trp Ile Glu Ser Lys Ile Phe
            20                  25                  30
Val Ile Gln Phe Trp Glu Met Ser Gln
35              40

SEQ ID NO: 17    FIG. 32

Met Leu Met Met Asp Thr Leu Tyr Asp Trp Leu Ile Asp Gly Phe Thr
1               5                   10                  15
Trp Leu Val Ile Lys Leu Gly Ile Met Trp Ile Ala Ser Lys Ile Phe
            20                  25                  30
Val Ile Gln Phe Phe Trp Glu Met Ser Gln
35                  40

SEQ ID NO: 18    FIG. 33

Met Leu Met Met Asp Thr Leu Tyr Asp Trp Leu Ile Asp Gly Phe Thr
1               5                   10                  15

Trp Leu Val Ile Ala Leu Gly Ile Met Trp Ile Ala Ser Lys Ile Phe
            20                  25                  30

Val Ile Gln Phe Phe Trp Glu Met Ser Gln
            35              40

SEQ ID NO: 19

FIG.34

ACCESSORY CHOLERA ENTEROTOXIN AND ANALOGS THEREOF AS ACTIVATORS OF CALCIUM DEPENDENT CHLORIDE CHANNEL

CROSS REFERENCE TO RELATED APPLICATIONS

This application is a 371 of PCT/US01/23530, filed Jul. 27, 2001; which claims benefit under 35 U.S.C. § 119(e) to U.S. Provisional Application No. 60/222,110, filed Jul. 28, 2000. The disclosure of which is incorporated herein by reference.

STATEMENT REGARDING FEDERALLY SPONSORED RESEARCH OR DEVELOPMENT

The research for the present invention was supported by a grant from the National Institutes of Health (grant number R29-AI-35717). The federal government has certain rights to this invention.

BACKGROUND OF THE INVENTION

1. Field of Invention

This invention relates to the use of the *Vibrio cholerae* accessory cholera enterotoxin (Ace) and Ace analogs as novel activators of the calcium-dependent chloride channel. More particularly, this invention relates to the use of Ace and Ace analogs to treat diseases involving insufficient chloride transport or insufficient bicarbonate transport, such as cystic fibrosis.

2. Introduction to Cystic Fibrosis

Cystic fibrosis (CF) is the most common genetic disease in Caucasian populations, with an incidence of 1 in 2,000 live births and a carrier frequency of approximately 1 in 20. It is inherited as an autosomal recessive disease. The cystic fibrosis gene has been mapped, cloned, and sequenced (Rommens et al., *Science* 245:1059-1065 (1989); Kerem et al., *Science* 245:1073-1080 (1989)). The gene product is the cystic fibrosis transmembrane regulator (CFTR) which functions as a chloride ion channel in the apical membranes of secretory epithelial cells (Anderson et al., *Science* 251:679-682 (1991)). The expression of the CFTR is most prominent in sweat glands and the respiratory and gastrointestinal tracts (Collins, F. S., *Science* 256:774-779 (1992)). CF is a disease of the epithelial cells, and the distribution of CFTR is essentially consistent with the clinical pathology.

In CF, the functionally defective apical membrane chloride channel secondarily leads to a loss of luminal sodium and water. In airways, the increase in sodium absorption and reduction in chloride secretion both lead to a loss of airway surface water. Thus, airway mucus is inspissated because of insufficient endobronchial water. Bronchiolar plugging and decreased mucociliary clearance follow. These changes in the pulmonary environment result in an increase in bacterial colonization. The colonization of the lung leads to a cycle of inflammation, destruction, and further colonization. The microorganisms colonizing the lungs attract neutrophils which contain and resolve a pulmonary infection in the normal host. However, in the patient with CF, the release of proteolytic enzymes by neutrophils further damages lung parenchyma. Neutrophils release neutrophil elastase which causes many typical pathologic features of CF, including epithelial damage, bronchial gland hyperplasia (leading to increased mucus production), and connective tissue damage resulting in bronchial distortion (Stockley et al., *Clin. Sci.* 74:645-650 (1988)). Neutrophils also release serine protease, a factor that damages bronchial cilia (Cole, P. J., *Eur. J. Respir. Dis.* 69(suppl 147):6-15 (1986)). The damaged bronchial cilia have decreased ciliary beat frequency and a reduction in mucociliary clearance. In the normal host, neutrophil proteases are controlled by the naturally occurring protease inhibitors found in the pulmonary tree. The most potent of these, alpha-1-antitrypsin, irreversibly binds with high affinity to serine protease. However, in the lung of the patient with CF, proteases are produced by a variety of cells besides neutrophils, including pulmonary macrophages and the microorganism, *Pseudomonas aeruginosa* (Fick et al., *Chest* 95:215S-216S (1989)). This excessive protease production overwhelms the naturally occurring endogenous protease inhibitors.

As a result of these physiological changes, respiratory tract diseases are responsible for more than 90% of the morbidity and mortality in CF (Hata et al., *Clin. Chest Med.* 9:679-689 (1988)).

The mainstays of treatment of cystic fibrosis are antibiotics for clinical exacerbations of pulmonary infection, aggressive physiotherapy and bronchodilators to increase the rate of secretion removal, and proper nutrition. (Hata et al., (1988)). There are also a number of new modalities which are under investigation. These include gene therapy (Drumm et al., *Cell* 62:1227-1233 (1990)), corticosteroids (Rosenstein et al., *Pediatrics* 87:245-246 (1991)), nonsteroidal anti-inflammatory agents (Konstan et al., *Am. Rev. Respir. Dis.* 141:186-192 (1990)), treatment with alpha-1-antitrypsin (McElvaney et al., *Lancet* 337:392-394 (1991)), and DNase (Elms et al., *Thorax* 8:295-300 (1953)). However, none of these treatment modalities are effective for long-term survival of the CF patient.

Description of Defect in Cystic Fibrosis

The basic defect in CF centers around abnormal ion transport. Two ions which appear to have defective transport in the affected CF epithelial cell are sodium and chloride. In the normal epithelial cell sodium is absorbed and chloride is secreted. This movement of sodium and chloride is accompanied by the movement of water. In the affected CF epithelial cell, sodium is hyper-absorbed into the cell, taking with it water from the airways. Because chloride secretion is defective, normal chloride and water secretion into the airways is blocked. This defect in ion transport leads to a decrease in airway fluid and thickened secretions. (Dinwiddie, R. *Respiration* 67:3-8 (2000)).

In the intestinal tract, three primary signal transduction mechanisms, the second messengers cAMP, cGMP or calcium, have been associated with the stimulation of epithelial chloride secretion (Dharmsathaphorn et al., *Methods in Enzymology: Biomembranes*, S. Fleischer and B. Fleischer (eds.), p. 354-389, Academic Press, Inc., San Diego (1990)). Activation of apical chloride secretion by either cyclic nucleotide is similar except that cAMP-dependent stimuli are generally more potent than cGMP-dependent stimuli. Cyclic nucleotides stimulate apical membrane chloride transport through the cystic fibrosis transmembrane regulator (CFTR) (Anderson et al., *Proc. Natl. Acad. Sci. USA* 88:6003-6007 (1991)). The calcium-dependent chloride secretory mechanisms appear to diverge and are less well defined. For example, histamine, serotonin and carbachol (an analog of acetylcholine, a critical neurohormone in the enteric nervous system) all increase intracellular calcium in intestinal epithelial cells but the characteristics of each response differs (Dharmsathaphorn et al., *Am. J. Physiol.* 256:C1224-C1230 (1989)).

Activation of calcium-dependent chloride secretion was thought, until recently, to be stimulated primarily through opening of $Ca^{2+}$-activated $K^+$ channels (Devor et al., *Am. J. Physiol.* 258:C318-C326 (1990)) which by increasing the negative intracellular potential increases the driving force for apical membrane chloride secretion. Recently, the presence of a distinct $Ca^{2+}$-dependent chloride channel (CaCC) in the apical membrane of polarized T84 cells was described (Merlin et al., *Am. J. Physiol.* 275:C484-C495 (1998)), although the molecular identity of the channel remains undefined.

It was first noted in the late 1980's (Dharmsathaphorn et al., *J. Clin. Invest.* 77:348-354 (1986); Dharmsathaphorn et al., (1989)) that calcium-dependent responses in intestinal epithelial cells were short-lived unlike most cyclic nucleotide-dependent responses. Barrett hypothesized that additional inhibitory second messengers antagonize the effects of calcium within the epithelial cell and that this accounts for the termination of the calcium-dependent chloride secretory response (Barrett, K. E., *Am. J. Physiol.* 41:C1069-C1076 1997)). Her laboratory and that of Traynor-Kaplan have been at the forefront of investigations to define the 'negative pathways' stimulated by carbachol, a prototypic calcium-dependent chloride secretagogue and have identified intracellular messengers which appear to negatively influence calcium-mediated chloride secretion. These include: influx of extracellular calcium, generation of inositol (3,4,5,6)-tetrakisphosphate ($IP_4$) (Kachintorn et al., *Am. J. Physiol.* 264:C671-C676 (1993)), activation of protein kinase C (Barrett, K. E., (1997)), and a tyrosine kinase-dependent signaling pathway (Keely et al., *J. Biol. Chem.* 273:27111-27117 (1998); Uribe et al., *Am. J. Physiol.* 271:C914-C922 (1996)).

Thus the major clinical phenotype of cystic fibrosis results from an absence of normal cAMP-regulated chloride transport.

Despite this knowledge, no one has been able to use this information to develop a truly effective treatment for CF. Current treatments are aimed to prevent or treat the pulmonary infections and the adverse physiological consequences of those infections. But no treatment reverses the cystic fibrosis defect in ion transport which, in turn, would lead to normal levels of water within the lumen of the lungs. Preventing the desiccation of the lungs by overcoming the defective ion transport would allow patients with cystic fibrosis to avoid pulmonary infections. Thus, there is a great need for a therapy to overcome or alleviate the defect in ion transport.

*Vibrio cholerae* accessory cholera enterotoxin (Ace) was initially described in 1993 as a toxin which increased short circuit current ($I_{sc}$) and potential difference (PD) in rabbit ileum mounted in Ussing chambers and caused fluid secretion in ligated rabbit ileal loops (Trucksis et al., *Proc. Natl. Acad. Sci. USA* 90:5267-5271 (1993)). At that time, the DNA sequence of Ace was determined and compared to CFTR. The comparison revealed a certain degree of homology between CFTR and Ace (Trucksis et al., (1993)). As such, it was hypothesized that Ace was a chloride ion channel and could replace CFTR in cystic fibrosis patients. More recent data suggests that Ace is not a chloride ion channel and thus could not act as a replacement channel for the defective CFTR in cystic fibrosis patients.

This invention overcomes the problems in the prior art. This invention provides a treatment for cystic fibrosis and other diseases having abnormal chloride or bicarbonate secretion by the usage of Ace or an Ace analog to activate the calcium-dependent chloride channel (CaCC), thereby stimulating the secretion of chloride and bicarbonate out of the cell. This stimulation of chloride secretion through an alternate chloride channel overcomes the defect in cystic fibrosis and other diseases involving a defective CFTR and/or defective chloride or bicarbonate transport.

BRIEF SUMMARY OF THE INVENTION

It is an object of this invention to use *Vibrio cholerae* accessory cholera enterotoxin (Ace) or an Ace analog to treat cystic fibrosis.

It is another object of this invention to use Ace or an Ace analog to increase the amount of airway surface water in the lungs by increasing the amount of calcium-dependent chloride secretion in the lungs in an animal. It is another object of this invention to increase the amount of airway surface water in the lungs in an animal by administering Ace or an Ace analog. It is a further object of this invention that the animal can be a mammal. It is a further object of this invention that the animal be a human.

It is an object of this invention to use Ace or an Ace analog to stimulate the activity of the calcium-dependent chloride channel and thus to increase the amount of chloride secreted into the lumen of the lungs of an animal. It is a further object of this invention to increase the amount of water passively transported into the lungs by increasing the amount of chloride secreted from the respiratory epithelial cells by administering Ace or an Ace analog.

It is another object of this invention to decrease the likelihood of bacterial infections in the lungs of cystic fibrosis patients by administrating Ace or an Ace analog. It is a further object of this invention that the administration of Ace increases the activity of cilia in the lungs and prevents bronchiolar plugging and decreased mucociliary clearance.

It is an object of this invention to administer Ace or an Ace analog to cystic fibrosis patients to prevent bacterial infections in the lungs.

It is an object of this invention to administer a pharmaceutical composition containing Ace or an Ace analog and a pharmaceutically acceptable carrier to cystic fibrosis patients. It is a further object of the invention that the administration of the pharmaceutical composition elevates chloride secretion in the lungs of cystic fibrosis patients to a higher level compared to non-treated cystic fibrosis lungs. It is a further object of this invention that the elevated level of chloride secretion is sufficient to permit the lungs to have enough airway surface water to prevent or reduce injury from pathogenic infections.

It is an object of this invention to have a method of treating cystic fibrosis patients with a compound to prevent pulmonary infections. It is a further object of this invention that the compound increases the airway surface water and ciliary action in the lungs of cystic fibrosis patients. It is a further object of this invention that the compound to be used in this method be Ace or an Ace analog.

It is an object of this invention to use Ace or an Ace analog to treat diseases with abnormal chloride transport and/or abnormal bicarbonate transport. It is a further object of this invention to use Ace or an Ace analog to treat diseases with abnormal chloride transport and/or abnormal bicarbonate transport through a cyclic nucleotide-dependent chloride channel, the CaCC. It is a further object of this invention to use Ace or an Ace analog to treat Dent's disease, X-linked nephrolithiasis, X-linked recessive hypophosphatemic rickets, autosomal dominant myotonia congenita and autosomal recessive general myotonia. It is a further object of this invention to alleviate some of the symptoms of Dent's disease, X-linked nephrolithiasis, X-linked recessive hypophosphatemic rickets, autosomal dominant myotonia congenita and autosomal recessive general myotonia by increasing the amount of chloride transport and/or bicarbonate transport in cells by the administration of Ace or an Ace analog.

It is an object of this invention to administer a polypeptide, Ace or an Ace analog, to an animal having a disease characterized by a cystic fibrosis transmembrane regulator with decreased activity compared to normal cystic fibrosis transmembrane regulator activity. It is a further object of this invention that Ace or the Ace analog activates the calcium-dependent chloride channel (CaCC). It is a further object of this invention that the Ace analog can be K43* (SEQ ID NO: 5), K21A (SEQ ID NO: 8), E28A (SEQ ID NO: 10), MT1 (SEQ ID NO: 17), MT2 (SEQ ID NO: 18), and MT3 (SEQ ID NO: 19) or a combination of these polypeptides. It is a further object of this invention that the disease being treated is cystic fibrosis. It a further object of this invention that the animal be a mammal or human.

It is an object of this invention to treat cystic fibrosis in an animal by administering a polypeptide which activates the calcium-dependent chloride channel (CaCC). It is a further object of this invention that the polypeptide administered is either Ace or an Ace analog. It is a further object of this invention that the dosage of Ace or the Ace analog administered is the amount which results in between 0.2 μg and 500 μg of Ace or Ace analog polypeptide per $cm^2$ of bronchial surface area of the animal, more preferably between 0.5 μg and 10 μg of Ace or Ace analog polypeptide per $cm^2$ of bronchial surface area of the animal. It is another object of this invention that the animal be a mammal or human.

It is an object of this invention to increase the amount of airway surface water in the lungs of an animal by administering a polypeptide which activates the calcium-dependent chloride channel (CaCC). It is a further object of this invention that the polypeptide be either Ace or an Ace analog. It is another object of this invention that the Ace analog used can be K43* (SEQ ID NO: 5), K21A (SEQ ID NO: 8), E28A (SEQ ID NO: 10), MT1 (SEQ ID NO: 17), MT2 (SEQ ID NO: 18), or MT3 (SEQ ID NO: 19) or a combination of these polypeptides.

It is another object of this invention to administer a polypeptide which activates the calcium-dependent chloride channel (CaCC) to an animal having a disease characterized by a cystic fibrosis transmembrane regulator having decreased activity compared to the activity of a normal cystic fibrosis transmembrane regulator and which results in a reduction in amount of airway surface water in the lungs of the animal. It is a further object of this invention that the animal have an increase in the amount of airway surface water in its lungs after administration of the polypeptide. It is another object of this invention that the polypeptide administered is either Ace or an Ace analog.

It is another object of this invention to increase the ciliary activity in the lungs of an animal having reduced ciliary activity by the administration of a polypeptide that activates the calcium-dependent chloride channel (CaCC). It is another object of this invention that the reduced ciliary activity is caused by, in part, a cystic fibrosis transmembrane regulator having decreased activity compared to the activity of a normal cystic fibrosis transmembrane regulator. It is another object of this invention that the polypeptide be either Ace or an Ace analog.

It is an object of this invention to administer Ace or an Ace analog to an animal having reduced ciliary activity in the lungs in order to increase the ciliary activity in the lungs of the animal. It is a further object of this invention that the reduced ciliary activity is caused by a decrease in the amount of chloride being secreted from bronchial epithelial cells. It is a further object of this invention that the dosage of Ace or the Ace analog administered is the amount which results in between 0.2 μg and 500 μg of Ace or Ace analog polypeptide per $cm^2$ of bronchial surface area of the animal, more preferably between 0.5 μg and 10 μg of Ace or Ace analog polypeptide per $cm^2$ of bronchial surface area of the animal. It is another object of the invention that the animal is a mammal, more preferably a human.

It is an object of this invention to increase chloride secretion from bronchial epithelial cells in the lungs of an animal having reduced chloride secretion from bronchial epithelial cells by administering a polypeptide that activates the calcium-dependent chloride channel to the animal. It is a further object of this invention that the polypeptide administered is either Ace or an Ace analog. It is another object of this invention that one administers either one or more of the following polypeptides along with a pharmaceutically acceptable carrier: K43* (SEQ ID NO: 5), K21A (SEQ ID NO: 8), E28A (SEQ ID NO: 10), MT1 (SEQ ID NO: 17), MT2 (SEQ ID NO: 18), and MT3 (SEQ ID NO: 19).

It is an object of this invention to administer a polypeptide to an animal whereby the polypeptide causes an increase in the amount of chloride and/or bicarbonate being secreted from cells. It is a further object of this invention that the animal has a disease characterized by a reduction in the amount of chloride and/or bicarbonate being secreted from cells. It is another object of this invention that the animal be a mammal, more preferably a human. It is a further object of this invention that the polypeptide administer be either Ace or an Ace analog. It is a further object of this invention that the animal have one of the following diseases: cystic fibrosis, Dent's disease, X-linked nephrolithiasis, X-linked recessive hypophosphatemic rickets, autosomal dominant myotonia congenita, and autosomal recessive general myotonia.

It is an object of this invention to have a composition of at least one polypeptide that activates the calcium-dependent chloride channel (CaCC) and at least one inhalation adjuvant. It is a further object of this invention that the polypeptide is Ace or an Ace analog.

It is an object of this invention to have a pharmaceutical composition for the treatment of a disease characterized by a decrease of chloride secretion by the cystic fibrosis transmembrane regulator, the composition being the polypeptide Ace (SEQ ID NO: 2) and a pharmaceutical acceptable carrier. It is an object of this invention that the disease can be cystic fibrosis, Dent's disease, X-linked nephrolithiasis, X-linked recessive hypophosphatemic rickets, autosomal dominant myotonia congenita, or autosomal recessive general myotonia.

It is an object of this invention to have a pharmaceutical composition for the treatment of a disease characterized by a decrease of chloride secretion by the cystic fibrosis transmembrane regulator, the composition being an Ace analog and a pharmaceutical acceptable carrier. It is another object of this invention that the Ace analog can be one or more of the following polypeptides: K43* (SEQ ID NO: 5), K21A (SEQ ID NO: 8), E28A (SEQ ID NO: 10), MT1 (SEQ ID NO: 17), MT2 (SEQ ID NO: 18), and MT3 (SEQ ID NO: 19). It is an object of this invention that the disease can be cystic fibrosis, Dent's disease, X-linked nephrolithiasis, X-linked recessive hypophosphatemic rickets, autosomal dominant myotonia congenita, or autosomal recessive general myotonia.

BRIEF DESCRIPTION OF THE DRAWINGS

FIG. 1A is the time course of $I_{sc}$ response. FIG. 1B is the time course of PD response. FIG. 1C is the time course of resistance response.

FIG. 3C shows the time course of $I_{sc}$ response of T84 cells to purified Ace monomer at varying concentrations.

FIG. 16 is the DNA sequence of Ace (SEQ ID NO: 1).

FIG. 17 is the amino acid sequence of Ace (SEQ ID NO: 2).

FIG. 18 is the amino acid sequence of L74*, an Ace analog (SEQ ID NO: 3).

FIG. 19 is the amino acid sequence of 158*, an Ace analog (SEQ ID NO: 4).

FIG. 20 is the amino acid sequence of K43*, an Ace analog (SEQ ID NO: 5).

FIG. 21 is the amino acid sequence of Q35*, an Ace analog (SEQ ID NO: 6).

FIG. 22 is the amino acid sequence of K43A, an Ace analog (SEQ ID NO: 7).

FIG. 23 is the amino acid sequence of K2IA, an Ace analog (SEQ ID NO: 8).

FIG. 24 is the amino acid sequence of K3OA, an Ace analog (SEQ ID NO: 9).

FIG. 25 is the amino acid sequence of E28A, an Ace analog (SEQ ID NO: IO).

FIG. 26 is the amino acid sequence of E39A, an Ace analog (SEQ ID NO: 11).

FIG. 27 is the amino acid sequence of M1A, an Ace analog (SEQ ID NO: 12).

FIG. 28 is the amino acid sequence of M3A, an Ace analog (SEQ ID NO: 13).

FIG. 29 is the amino acid sequence of M4A, an Ace analog (SEQ ID NO: 14).

FIG. 30 is the amino acid sequence of K43D5, an Ace analog (SEQ ID NO: 15).

FIG. 31 is the amino acid sequence of D11, an Ace analog (SEQ ID NO: 16).

FIG. 32 is the amino acid sequence of MT1, an Ace analog (SEQ ID NO: 17).

FIG. 33 is the amino acid sequence of MT2, an Ace analog (SEQ ID NO: 18).

FIG. 34 is the amino acid sequence of MT3, an Ace analog (SEQ ID NO: 19).

DETAILED DESCRIPTION OF THE INVENTION

Figure 1A:
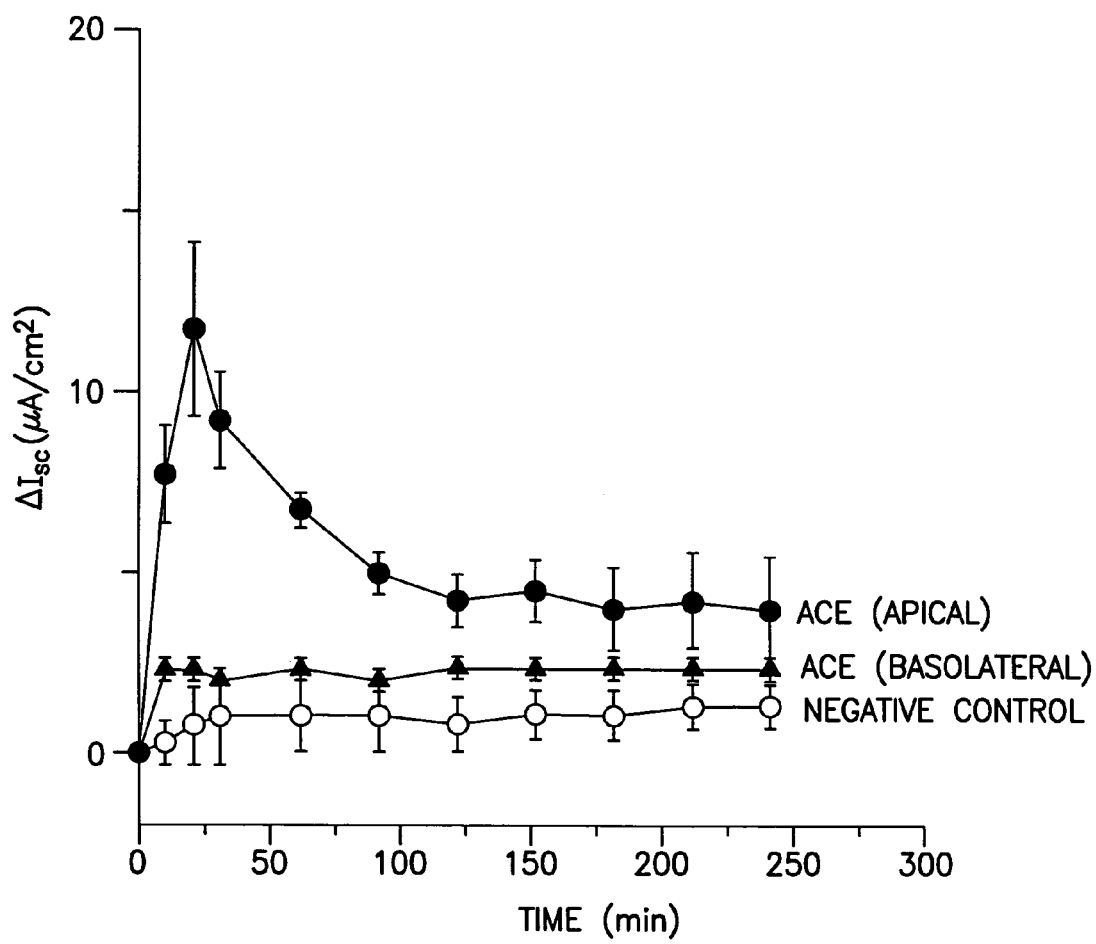
FIGS. 1A-1C illustrate the effects of *V cholerae* Ace⁺ and Ace⁻ culture supernatants on T84 cell monolayers in a Ussing chamber whereby the *V. cholerae* Ace⁺ culture supernate is applied to either the apical membrane or basolateral membrane.

This invention involves the treatment of cystic fibrosis with Ace or an Ace analog. Ace or an Ace analog can be administered to patients with cystic fibrosis to increase the level of chloride secretion within the lungs. This increase in chloride secretion results in water traveling into the lumen of the lungs and returning to a level sufficient to prevent damage to the lungs caused by the desiccation that normally occurs in cystic fibrosis patients. By having increased airway surface water levels compared to untreated cystic fibrosis patients, bronchiolar plugging and decreased mucociliary clearance are avoided. Thus, pathogenic infections are avoided and the lungs are not injured.

Ace and Ace analogs bypass the defective cAMP-activated CFTR chloride channel by activating the calcium-dependent chloride channel (CaCC), thereby returning chloride secretion back to normal levels. Ace potentiates the chloride secretory activity of carbachol by blocking a normal inhibitory pathway stimulated by carbachol.

The DNA and amino acid sequence for Ace has already been determined (Trucksis et al., (1993)). The DNA sequence of Ace is contained in FIG. 16 (SEQ ID NO: 1). The amino acid sequence of Ace is contained in FIG. 17 (SEQ ID NO: 2). The GenBank accession number is Z22569.

Mechanism of Action of Ace

To demonstrate that Ace stimulates the secretion of chloride from cells through the CaCC, the mechanism of action of Ace is examined in various cell lines. T84 cells, an epithelial cell line that secrete chloride, is derived from a human colonic carcinoma. T84 cells resemble crypt cells morphologically and secrete chloride in response to secretagogues whose actions are mediated via cAMP-, cGMP- or $Ca^{2+}$-related mechanisms (Dharmsathaphorn et al., (1990)).

16HBE14o- cells are a human airway epithelial cell line that expresses both the CFTR and CaCC; both channels secrete chloride. 16HBE14o- cells are derived from a 1 year old male heart-lung transplant patient by transformation by calcium phosphate transfection with the pSVori- plasmid (Cozens et al., *Am.J.Respir. Cell Mol. Biol.* 10:38-47 (1994)). This cell line retains tight junctions and directional chloride ion transport. The cells increase chloride transport in response to either cyclic nucleotide agonist or calcium ionophores which indicates the presence of functional CFTR and CaCC. The presence of CFTR at both the mRNA and protein level has been identified by Northern and Western hybridization analysis, respectively (Cozens et al., *Am.J.Respir. Cell Mol. Biol.* 10:38-47 (1994)).

CFBE41o- is a human airway epithelial cell line that contains a mutation in the CFTR gene. Transformed with the pSVori- plasmid, CFBE41o- cells are homozygous for mutant CFTRΔF508 (Meng, et al., J. Pathol. 184: 323-331 (1998)). CFTRΔF508 is the most common mutation in CF and results in a partially functional chloride channel with a decreased probability of being open. The mutation causes the retention of the CFTR in the endoplasmic reticulum so that it does not traffic properly to the plasma membrane. Thus CFBE41o- is an excellent model for how airway epithelial cells in CF patients function.

Materials. Cholera toxin, E. coli heat stable enterotoxin, carbachol, collagen, bumetanide, 1,2-bis(2-aminophenoxy) ethane-N,N,N',N'-tetraacetic acid (BAPTA)-AM, nifedipine, verapamil, ω-conotoxin GVIA, clotrimazole, dantrolene, staurosporine, 4,4'-diisothiocyanostilbene-2,2'-disulfonic acid, sodium (DIDS), nystatin, genistein and thapsigargin are obtained from Sigma Chemical Company (Sigma-Aldrich, St. Louis, Mo.). Forskolin is obtained from Calbiochem-Novabiochem Corporation (San Diego, Calif.).

Figure 3A:
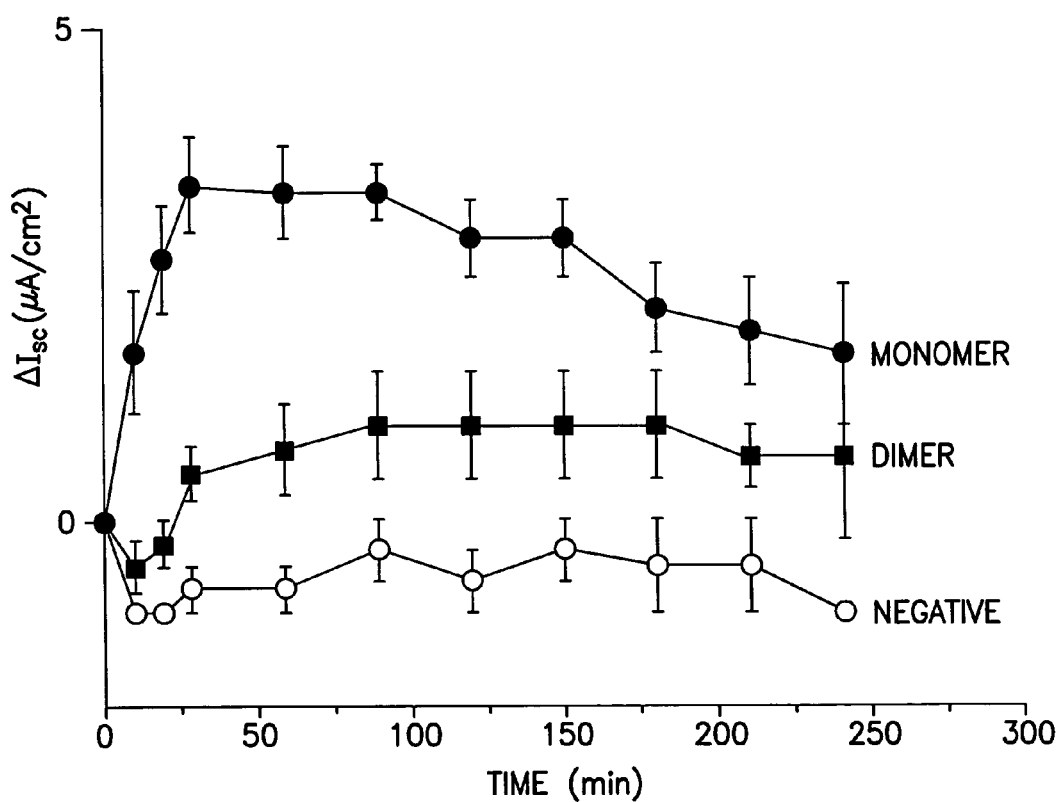
FIG. 3A shows the time course of $I_{sc}$ response to purified Ace monomer and dimer and Ace⁻ culture supernatant by T84 monolayers in the Ussing chamber.
Figure 3B:
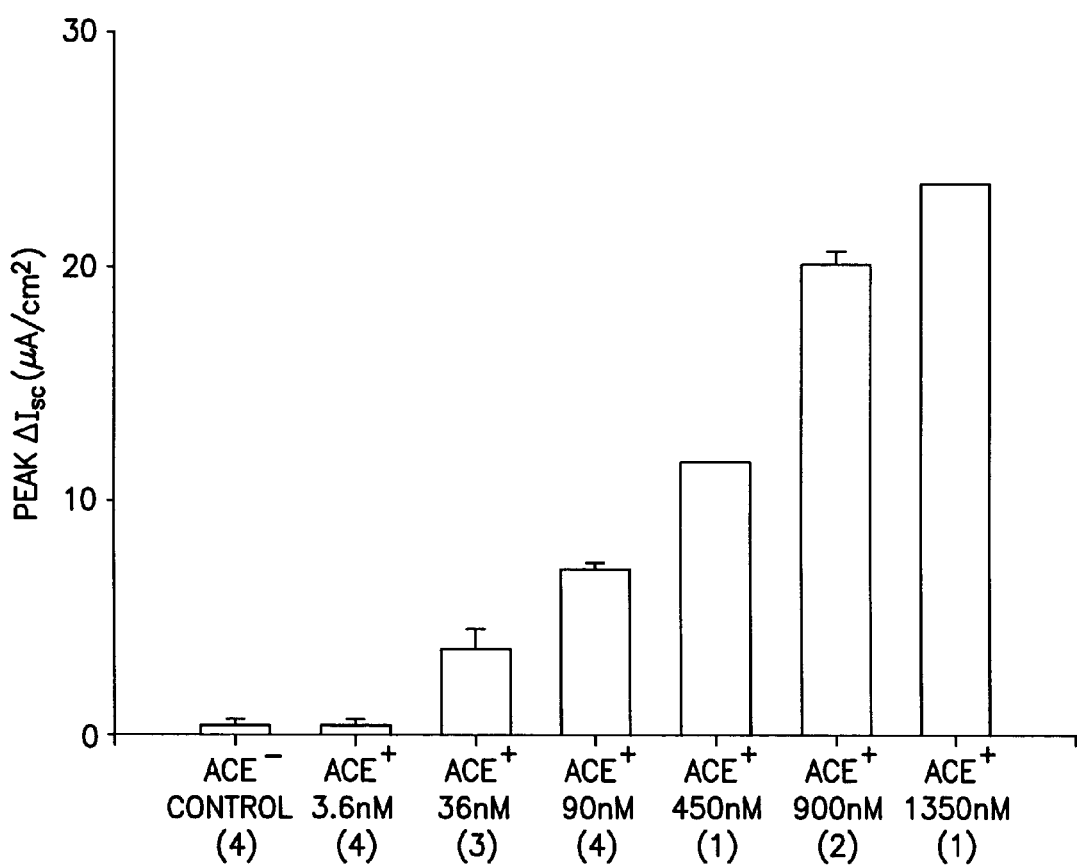
FIG. 3B illustrates the concentration-response of T84 cells with Ace toxin.

Ace preparation. Cultures of V. cholerae bacterial strains Ace$^-$ (CVD113, CT$^-$, Zot$^-$, Ace$^-$) (Fiore et al., Infect. Immun. 65:3112-3117 (1997)) and Ace$^+$[CVD113 (pCVD630, Ace$^+$)] (Fiore et al. (1997); Trucksis et al., (1993)) are grown in L broth at 37° C. with shaking. Culture supernatants are prepared by centrifugation followed by filtration through a 0.45 μm filter. The filtered supernatant is then fractionated and concentrated 1000-fold using Pall Filtron Omega stir cells (Pall Filtron Corp., Northborough, Mass.) to obtain a 5000 to 30,000 $M_r$ fraction. The fraction is washed and resuspended in PBS. The partially purified Ace$^+$ and Ace$^-$ supernatants are used for all experiments except where noted. The concentration of Ace in the partially purified supernatants is estimated at $4.5 \times 10^{-7}$ M based on a comparison of peak $\Delta I_{sc}$ induced by the partially purified supernatants in comparison to the peak $\Delta I_{sc}$ induced by using purified Ace toxin (FIG. 3B). Native purified Ace monomer (see below) is used in a subset of 1-2 experiments of each type to confirm that purified Ace gives the same results as the partially purified preparation. In addition, the concentration-response experiments (FIG. 3B) are performed with native purified Ace monomer. All samples are stored at −20° C. until tested in Ussing chambers.

Cell culture and filter preparation. T84 cells are grown in a 1:1 mixture of Dulbecco's modified Eagle's medium and Ham's F-12 nutrient supplement with 29 mM $NaHCO_3$, 20 mM HEPES, 50 U/ml penicillin, 50 μg/ml streptomycin, and 10% fetal bovine serum. T84 cells are plated onto collagen-coated Transwell polycarbonate inserts (Corning Costar Corp., Acton, Mass.) at a density of $7 \times 10^4$ cells/cm$^2$. Transepithelial resistances attain stable levels (>1000 Ω/cm$^2$) after 12 days.

The human bronchial cell lines 16HBE14o- and CFBE41o- (both obtained from Dr. Deiter Gruenert, University of Vermont, Burlington, Vt.) are grown in Eagle's minimal essential media (MEM) supplemented with 20 mM $NaHCO_3$, 2 mM L-glutarnine, 100 μg/ml streptomycin, 100 U/ml penicillin and 10% fetal bovine serum (FBS). Cells are maintained in tissue culture flasks coated with fibronectin, collagen and bovine serum albumin. For Ussing chamber experiments, cells are plated onto fibronectin, collagen and BSA coated 0.4 μm Transwell polycarbonate inserts (Corning Costar, Acton, Mass.). The cells are plated at a density of $1 \times 10^6$ cells per well in a 50:50 mixture of Dulbecco's modified Eagle's medium and Ham's F12 Nutrient Mixture (DMEM/F12) supplemented with 29 mM $NaHCO_3$, 20 mM HEPES, 10 μg/ml streptomycin, 10 U/ml penicillin and 10% FBS. All cells are maintained at 37° C., 5% $CO_2$. The cells reach a stable transepithelial resistance of 100-200 ohms/cm$^2$ after 5 days.

Ussing chamber voltage-clamp transport studies. Transepithelial transport studies are carried out across T84 cell, 16HBE14o- cell, or CFBE41o- cell confluent monolayers in a simplified apparatus for measuring electrophysiological parameters (surface area 1.0 cm$^2$) designed for study of filter-grown cells previously described by Madara et al. (Madara et al., J. Tiss. Cult. Meth. 14:210-216 (1992)). $I_{sc}$ and open-circuit PD measurements are carried out in culture media (except where noted to be in Ringer's or $Ca^{2+}$-, $HCO_3^-$- or $Cl^-$-free Ringer's) using Ag-AgCl and calomel electrodes via 4% agar bridges made with Ringer's buffer. The electrodes are connected to an automatic voltage clamp (DVC 1000, World Precision Instruments, New Haven, Conn.). The PD is recorded under open-circuit conditions every 10 minutes (or at shorter intervals as indicated), then the voltage is clamped and the $I_{sc}$ is recorded (Lencer et al., J. Clin. Invest. 92:2941-2951 (1993); Lencer et al., Am. J. Physiol. 269:G548-G557 (1995)). Resistance of the monolayers is calculated from the $I_{sc}$ and open-circuit PD according to Ohm's law. Ringer's solution contains (in mM): 140 $Na^+$, 25 $HCO_3^-$, 5.2 $K^+$, 1.2 $Ca^{2+}$, 1.2 $Mg^{2+}$, 119.8 $Cl^-$, 0.4 $H_2PO_4^-$, 2.4 $HPO_4^{2-}$, 10 glucose, and 5 HEPES, pH 7.4. For the $Cl^-$-free Ringer's, the NaCl is replaced by Na isethionate and the $CaCl_2$ and $MgCl_2$ are replaced by $CaSO_4$ and $MgSO_4$ at the same molarities. For the $HCO_3^-$-free Ringer's, the $NaHCO_3$ is replaced by Na isethionate. In experiments in which the effect of $Ca^{2+}$ on Ace secretory activity is examined, $Ca^{2+}$-free Ringer's (Fasano et al., Gastroenterol. 100:471-476 (1991)) with the following composition is used (in mM): 140 $Na^+$, 25 $HCO_3^-$, 5.2 $K^+$, 1.0 $Mg^{2+}$, 117 $Cl^-$, 0.4 $H_2PO_4^-$, 2.4 $HPO_4^{2-}$, 10 glucose, 5 HEPES and 1.0 EGTA, pH 7.4. The intracellular $Ca^{2+}$ chelator BAPTA-AM is loaded into the cells during a 1-hour pre-incubation period in Ringer's solution at the desired concentration.

Purification of native Ace toxin. Culture supernatant of wild type V. cholerae strain E7946 is fractionated using Pall Filtron Omega stir cells and a Mini Prep Cell (Bio-Rad Laboratories, Hercules, Calif.) as reported previously (Trucksis et al., Infect. Immun. 65:4984-4988 (1997)). Both the monomer and dimer forms of the Ace toxin are purified separately, as previously reported, and each yields a single band with silver-stain.

Measurement of cyclic nucleotides. Cells grown on Costar inserts are treated with Ace, forskolin, V. cholerae CT, E. coli STa, and carbachol at various concentrations. Intracellular cAMP is extracted with ice-cold 50% ethanol-50% Ringer solution (vol/vol). Extraction for cGMP measurements is performed with ice-cold 67% ethanol-33% Ringer solution (vol/vol). The cell extracts are frozen at −20° C. until assayed by cyclic nucleotide enzyme immunoassay (EIA, cAMP and cGMP) system (Amersham Life Science, Piscataway, N.J.) according to manufacturer's instructions.

Statistical Analysis. The effects of various treatments are analyzed by repeated-measures analysis of variance, where the dependent variable is PD or $I_{sc}$, independent variable is treatment group (treated vs. control), with time 0 as a covariate. Each of these analyses are tested for a group effect (i.e., mean difference in PD between treatment groups) and a group X time interaction (differential change in PD over time in the two groups). Data shown are mean ± the standard error. Statistical hypotheses are evaluated at the 5% level.

Figure 1B:
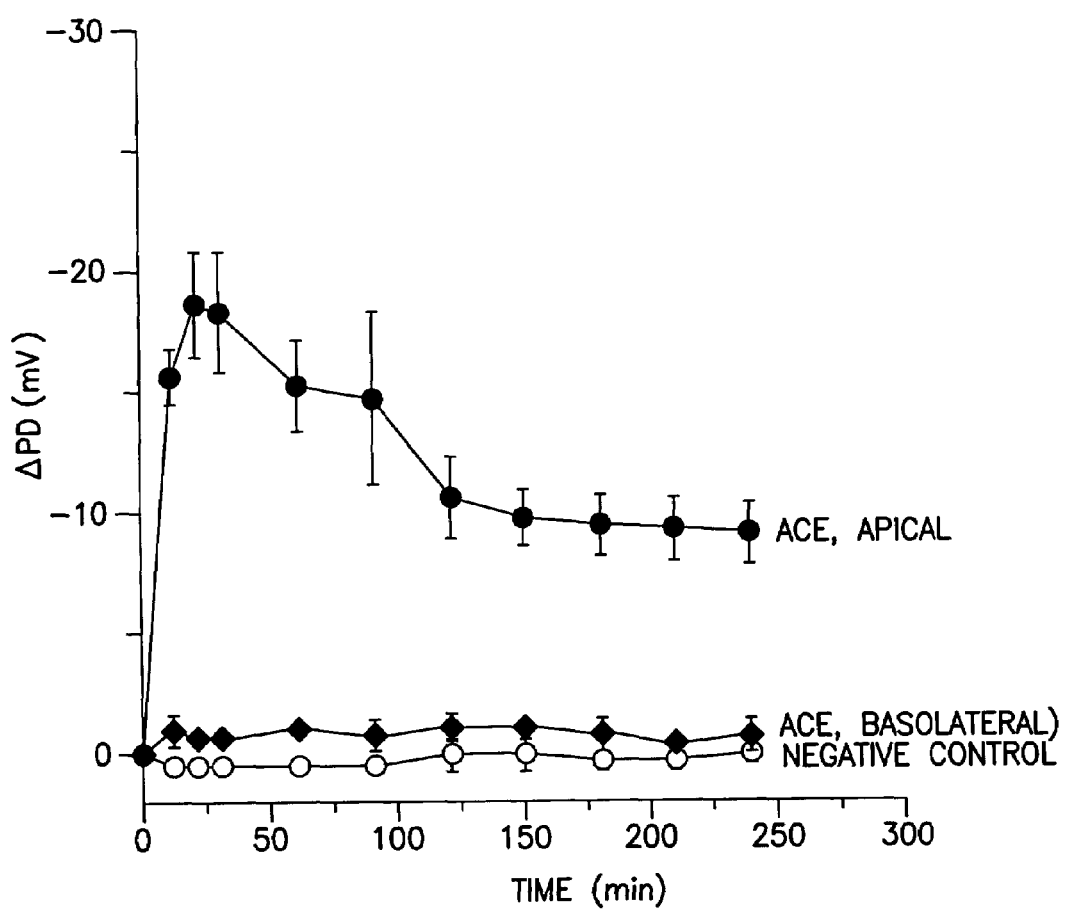

Ace stimulates a reversible increase in short circuit current and potential difference in T84 cell monolayers. The addition of Ace (in culture supernatant) to the apical bathing solution of T84 cell monolayers causes increases in $I_{sc}$ (FIG. 1A) and PD (FIG. 1B) as measured in modified Ussing chambers. Basolateral addition alone of Ace has no effect. Maximal response is reached by 20 minutes after the addition of Ace, and the effect persists for at least 2 hours. The peak $I_{sc}$ for supernatants of an Ace$^+$ V. cholerae strain compared to an Ace⁻ V. cholerae strain (negative control) are 11.8±2.4 µAmp/cm² vs. 0.8±1.1 µAmp/cm² (P=0.006, n=4, FIG. 1A). The peak PD values for supernatants of an Ace⁺V. cholerae strain compared to an Ace⁻V. cholerae strain (negative control) are −18.5±2.2 mV vs. 0.6±0.2 mV (P<0.001, n=4, FIG. 1B). (In FIG. 1A, "O" is Ace⁻ culture supernatant, apical side of cells; "●" is Ace⁺ culture supernatant, apical side of cells; "▲" is Ace⁺ culture supernatant, basolateral side of cells.) (In FIG. 1B, "O" is Ace⁻ culture supernatant, apical side of cells; "●" is Ace⁺ culture supernatant, apical side of cells; "♦" is Ace⁺ culture supernatant, basolateral side of cells.)

Figure 1C:
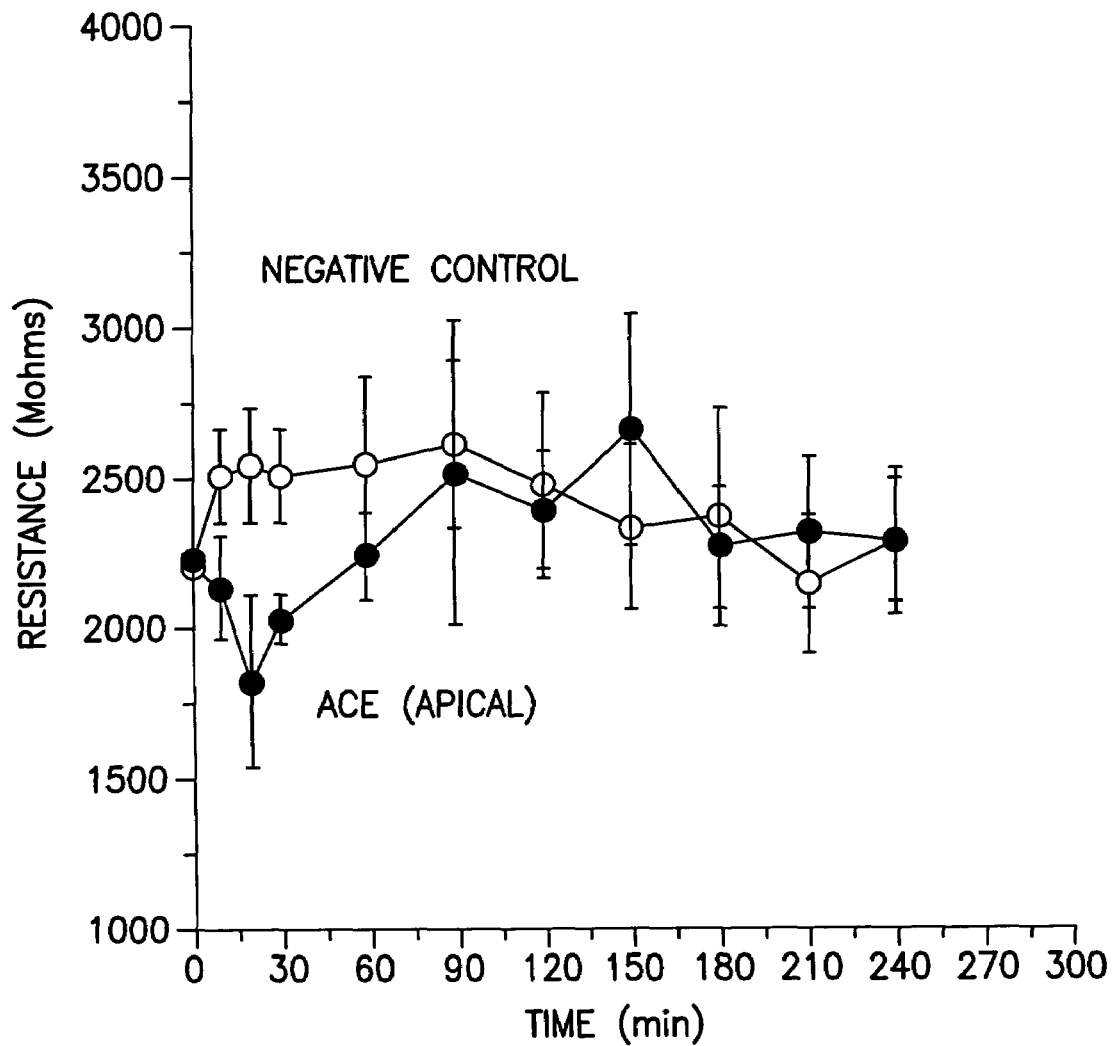

The increase in $I_{sc}$ and PD of an Ace⁺V. cholerae strain compared to an Ace⁻V. cholerae strain is significant throughout a 2 hour time course. Twenty minutes after the addition of apical Ace (but not basolateral) the resistance of T84 cell monolayers drops approximately 20% (P=0.08) and then returns to baseline by 60 minutes (FIG. 1C, "O" is Ace⁻ culture supernatant; " " is Ace⁺ culture supernatant; both being added to the apical side of the cells (n=4).)

All subsequent studies of Ace with T84 cells are performed with apical addition of Ace to the T84 cell monolayer. no basolateral addition of Ace.

Figure 2:
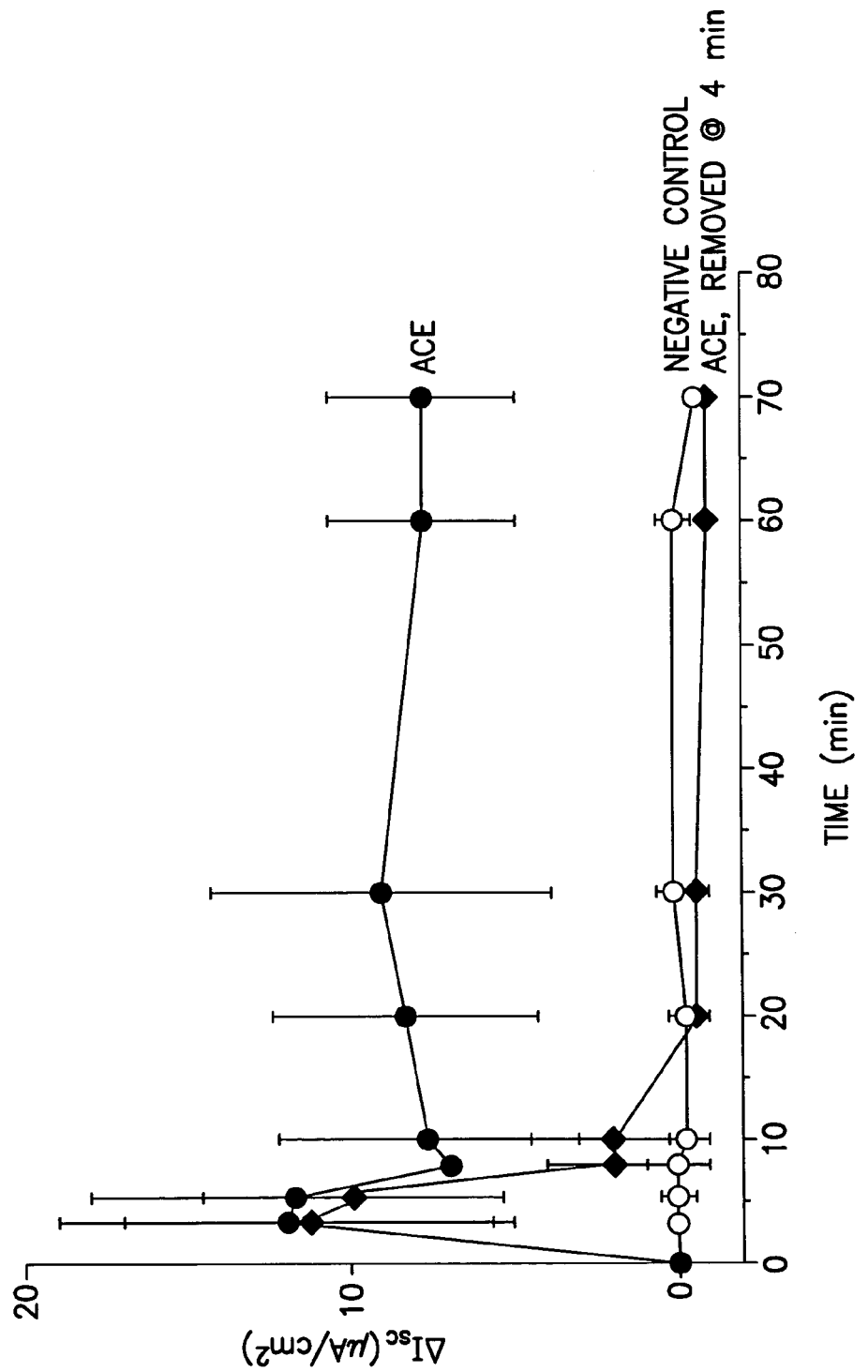
FIG. 2 shows the effect of the removal of Ace on Ace-induced $I_{sc}$ response by T84 cell-monolayers.

To determine whether the increase in the T84 cell monolayer's electrical parameters is reversible, the bathing media is replaced at different time points with Ace-free media after Ace stimulated increases in $I_{sc}$ and PD. The increase in $I_{sc}$ and PD induced by Ace is immediately and completely reversible whether removed after 4 minutes (see FIG. 2), 60 minutes or 120 minutes (data not shown). (In FIG. 2, "●" is Ace alone; "♦" is Ace removed at 4 minutes; and "O" is negative control (n=3).)

Purified Ace protein stimulates concentration-dependent increases in $I_{sc}$ and PD as seen with partially purified Ace⁺ culture supernatants. The Ace protein is purified from a wild type V. cholerae strain E7946. The predominant form of the Ace toxin produced in V. cholerae has a molecular weight of 18,000 Da representing an Ace dimer (Trucksis et al., (1997)). A second protein of molecular weight 9000 Da consistent with a monomer form of Ace is also present. When these proteins are analyzed on T84 cells, the monomer form of Ace produces a concentration-dependent increase in $\Delta I_{sc}$ compared to the negative control (FIG. 3B). The threshold concentration of purified Ace which induced a significant increase in $I_{sc}$ is approximately $10^{-8}$ M (36 nM) (P=0.008) with a maximal effect at approximately $10^{-7}$ M (900 nM) (FIG. 3B). Similar results were obtained when PD was analyzed (data not shown).

Because of limitations in the availability of purified Ace (Trucksis et al., (1997)), it is not possible to stimulate the monolayers with a high enough concentration of Ace to clearly saturate the $I_{sc}$ response. Thus, it is difficult to calculate the Ks. The time to peak $I_{sc}$ is concentration-dependent as increasing the concentration of toxin shifted the peak $I_{sc}$ to an earlier time. In FIG. 3C, 450 nM of purified Ace monomer (●) stimulates a higher and earlier peak $I_{sc}$ response (8 µA/cm² at 5 minutes) on T84 cell monolayers than does 36 nM of purified Ace monomer (O) (2.5 µA/cm² at 30 minutes).

The time-dependent PD, $I_{sc}$, and R responses of T84 monolayers to purified Ace are similar to that observed with the partially purified culture supernatant (see FIG. 1, data not shown). In FIG. 3A, the dimer form of Ace demonstrates less activity as measured by the $I_{sc}$ response than the monomer (Ace dimer "■" vs. negative control "O", P≦0.3 at 20, 30 and 60 minutes; P≧0.7, at 10 minutes and 90 to 240 minutes; Ace monomer " "; n=4). As illustrated in FIG. 3A, Ace monomer generates an $I_{sc}$ of >2.5 µA/cm² by 30 minutes, compared to <1 µA/cm² by 30 minutes by Ace dimer.

Ace-stimulated secretion is equally dependent on Cl⁻ or HCO₃⁻ ions. It has previously been shown that the loop diuretic, bumetanide, inhibits the basolaterally localized Na⁺/K⁺/2Cl⁻ cotransport system in the T84 cell line (Dharmsathaphorn et al., J. Clin. Invest. 75:462-471 (1985)). This transport pathway serves as the principal Cl⁻ uptake pathway and its inhibition by bumetanide results in a reversal or inhibition of Cl⁻ secretion mediated by cyclic nucleotides or Ca²⁺. Therefore, bumetanide is used to test the involvement of this cotransport pathway in the Cl⁻ secretory process activated by Ace.

Figure 4:
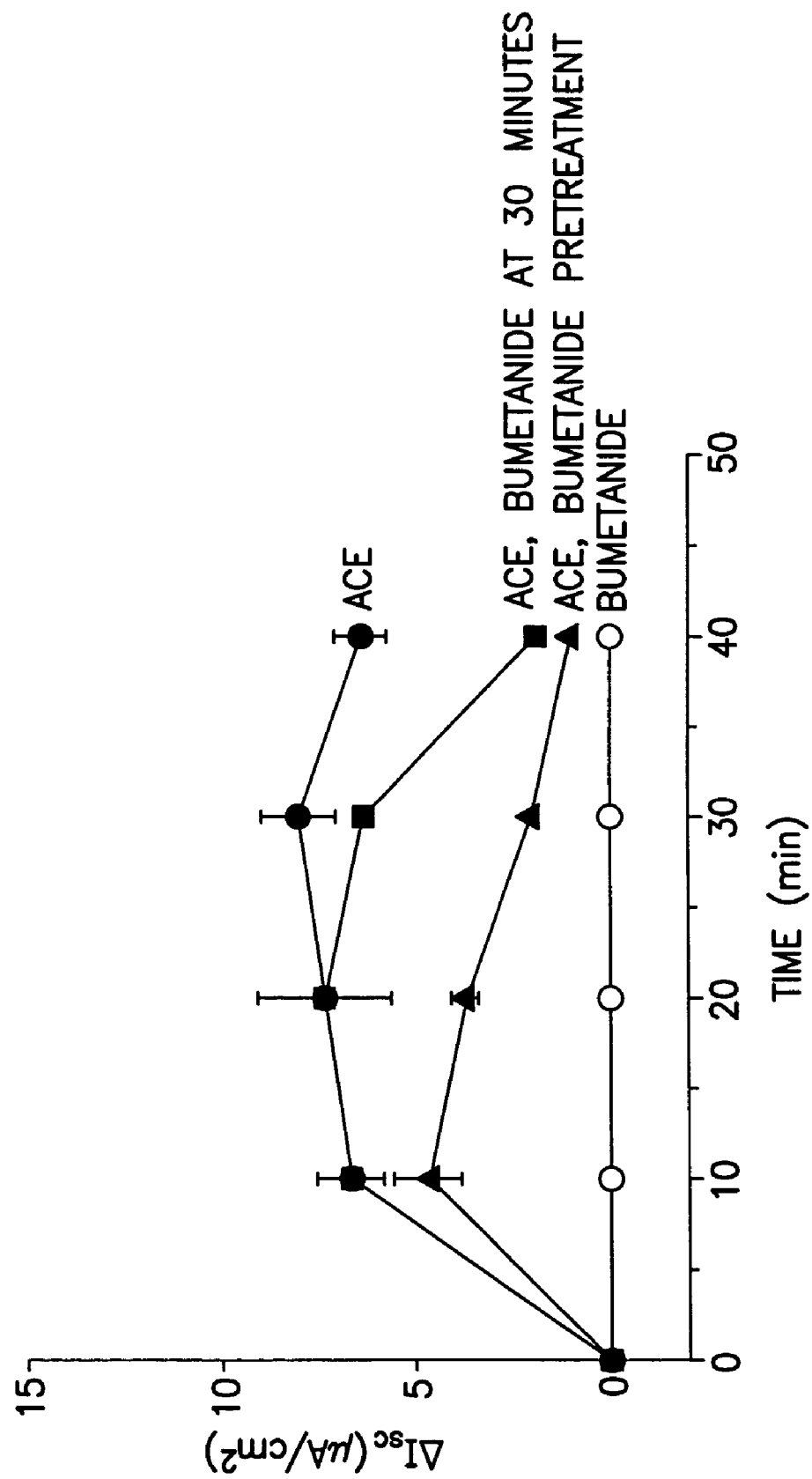
FIG. 4 illustrates the effect of bumetanide on Ace-induced $I_{sc}$ response by T84 cell monolayers.

As illustrated in FIG. 4, bumetanide (100 µM, added to the basolateral reservoir) substantially inhibits the Ace-induced $I_{sc}$ response of T84 cell monolayers (P=0.003, n=3). As is the case for $PGE_1$-induced Cl⁻ secretion (Weymer et al., J. Clin. Invest. 76:1828-1836 (1985)) and STa-induced Cl⁻ secretion (Huott et al., J. Clin. Invest. 82:514-523 (1988)), pretreatment (30 minutes) of T84 cell monolayers with bumetanide ($10^{-4}$ M, "▲") substantially (~60%), inhibits the action of Ace. Bumetanide, by itself ("O"), has no effect on $I_{sc}$ or PD. Bumetanide also reverses the action of Ace when added 30 minutes after Ace elicits a response ("■", bumetanide added at peak of Ace-induced $I_{sc}$ response). Similarly, ouabain (250 µM), which inhibits the Na⁺, K⁺-ATPase necessary for active transepithelial Cl⁻ secretion, inhibits and reverses Ace-induced $I_{sc}$ when added to the basolateral reservoir. The inhibition of Cl⁻ secretion by bumetanide demonstrates that Na⁺, Cl⁻, and possibly K⁺ are required for the Cl⁻-uptake step in Ace's action and that this process is localized to the basolateral membrane of the T84 cells.

Figure 5:
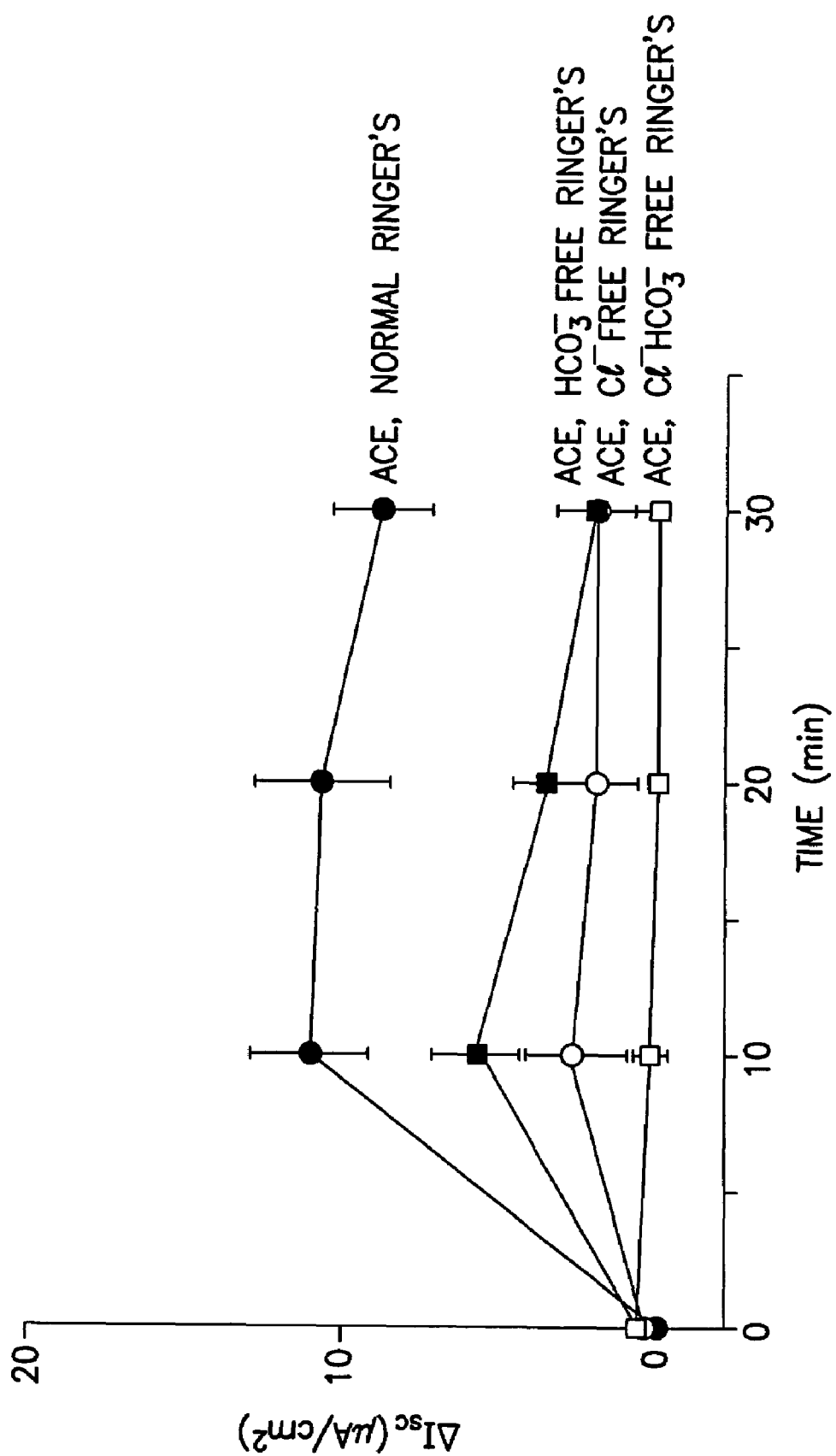
FIG. 5 shows the time course of $I_{sc}$ response to *V. cholerae* Ace⁺ culture supernatants by T84 cell monolayers in various buffers.

To verify the involvement of Cl⁻ and/or HCO₃⁻ in the Ace-stimulated increase in $I_{sc}$/PD, ion replacement studies are performed (FIG. 5). Of note, the peak of Ace activity ($I_{sc}$ in T84 cell monolayers) is approximately 60-80% inhibited when the Ringer's solution (" ") is replaced by Cl⁻-free Ringer's ("O", P=0.03), or when replaced by HCO₃⁻- free Ringer's ("■"). When both ions are removed from the Ringer's solution ("□"), there is complete inhibition of Ace-induced current (P=0.005).

The effect of Ace on second messengers. To explore further the mechanism of action of Ace, the effect of the enterotoxin on cellular cAMP and cGMP is measured. Ace and carbachol has no significant effect on cellular cGMP or cAMP, while STa increases cGMP but has no effect on cAMP and forskolin and V. cholerae CT increases cAMP but has no effect on cGMP.

Figure 6A:
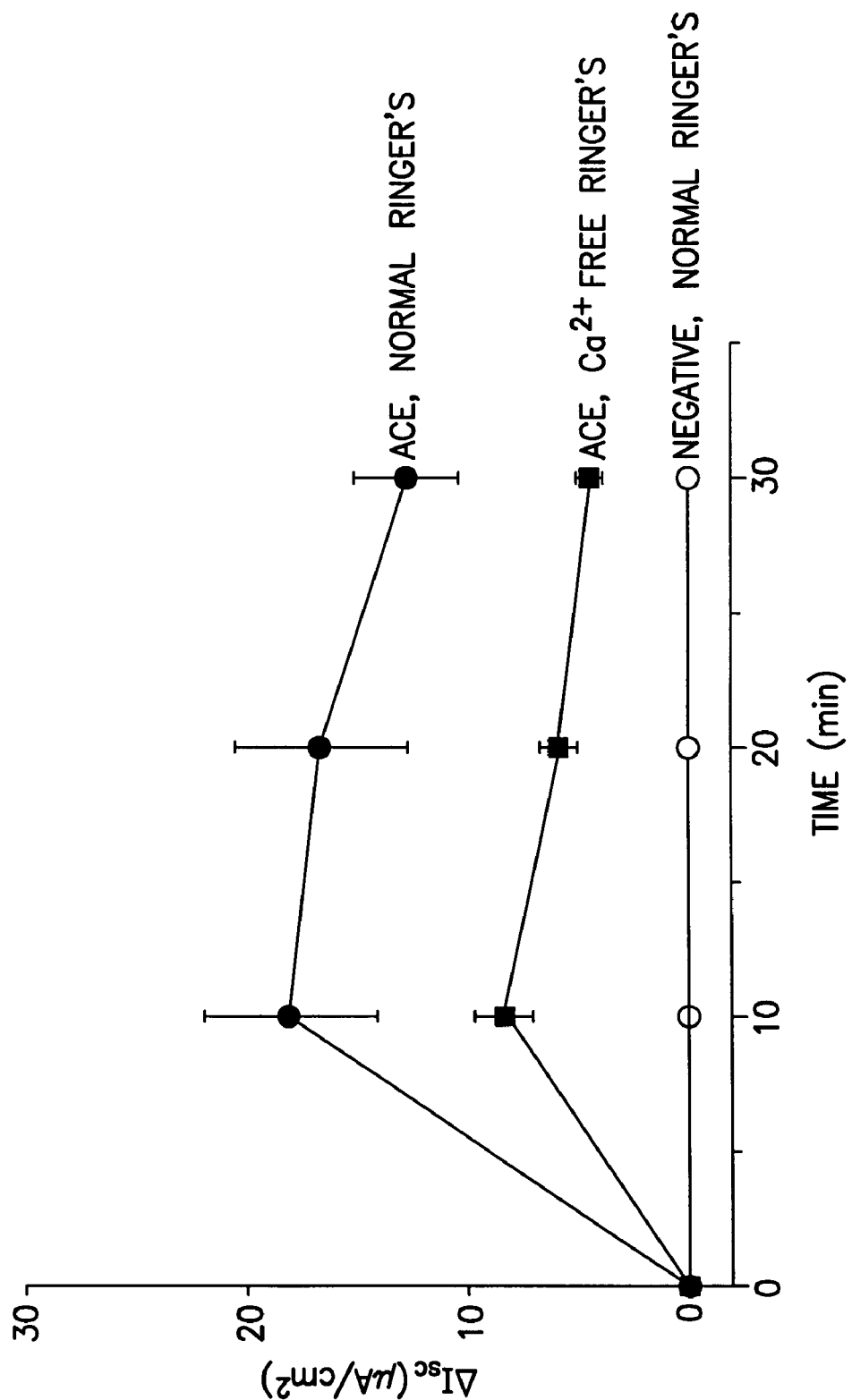
FIGS. 6A-E illustrate the calcium-dependence of Ace-induced $I_{sc}$ in T84 cell monolayers.

To examine the role of calcium as a second messenger, ion replacement studies are performed with T84 monolayer in the Ussing chamber with normal Ringer's solution replaced by Ca²⁺-free Ringer's in the apical reservoir 30 minutes prior to the addition of the Ace toxin. Ace is added at a near maximal concentration (90 to 900 nM). The basolateral reservoir retains normal Ringer's solution, which is required to maintain tight junction integrity (Unno et al., Am. J. Physiol. 274:G700-G708 1998)). As illustrated in FIG. 6A, the peak action of Ace is approximately 65% inhibited when the apical Ringer's solution ("●") is replaced by Ca²⁺-free Ringer's solution ("■"; n=5; P=0.04). The resistance of the T84 cell monolayers is unchanged as compared to the resistance of parallel controls in normal Ringer's solution ("O").

Figure 6B:
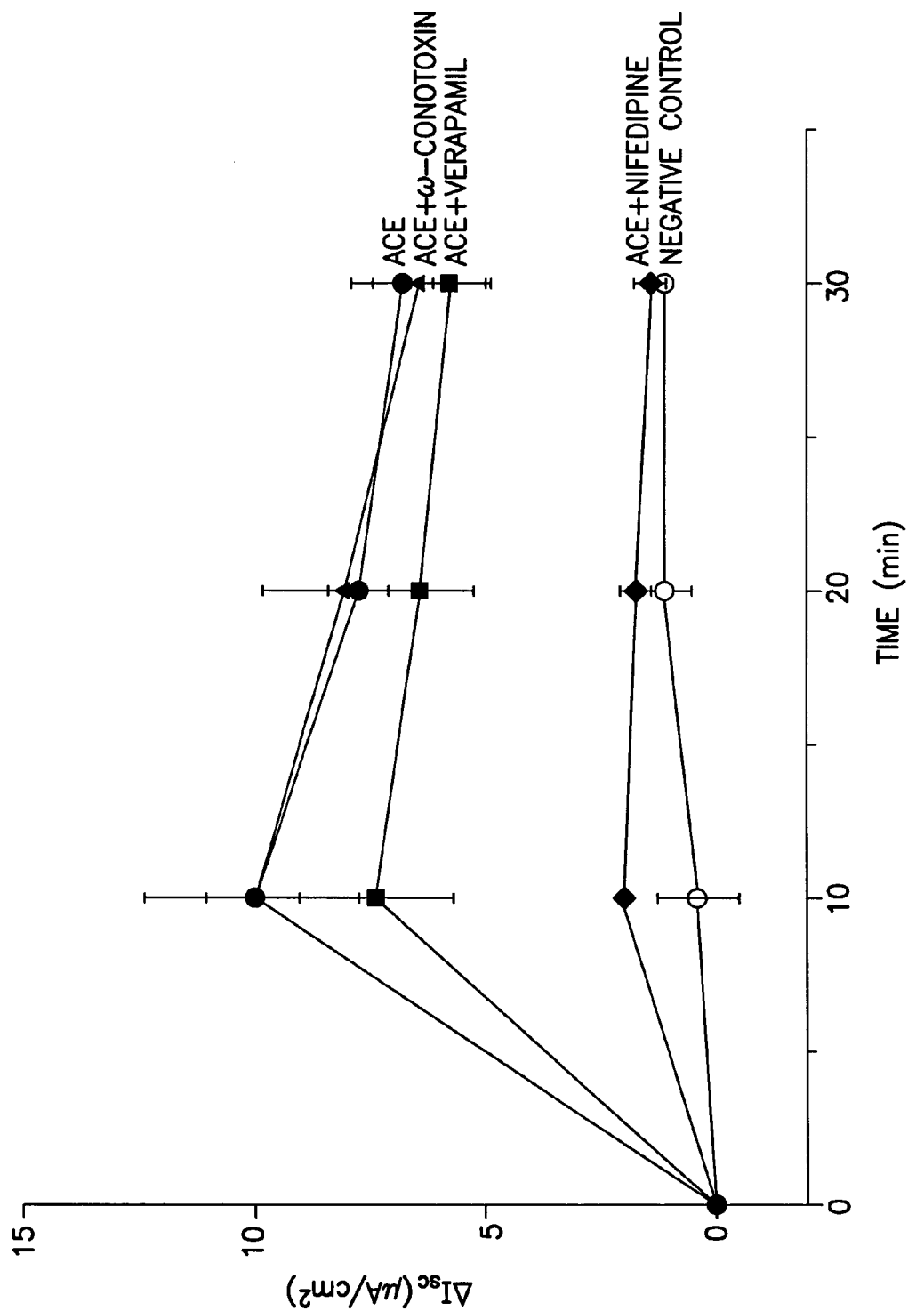

Furthermore, pretreatment of T84 cell monolayers with the calcium channel blocker, nifedipine (10 µM), inhibits the Ace-induced $I_{sc}$ response almost completely (FIG. 6B, "♦" is Ace+nifedipine, P=0.001). In contrast, pretreatment with the calcium channel blockers, ω-conotoxin (1 μM) and verapamil (10 μM) has no significant effect on the Ace-induced $I_{sc}$ response (FIG. 6B; "●" is Ace alone; "▲" is Ace+ω-conotoxin; "■" is Ace+verapamil; and "O" is the negative control.) These three calcium channel blockers are added to the apical bath 30 minutes before the addition of Ace. Interestingly, only nifedipine significantly inhibited Ace-induced $I_{sc}$, thus demonstrating that the apical influx of extracellular calcium is required for the Ace effect on $I_{sc}$.

Figure 6C:
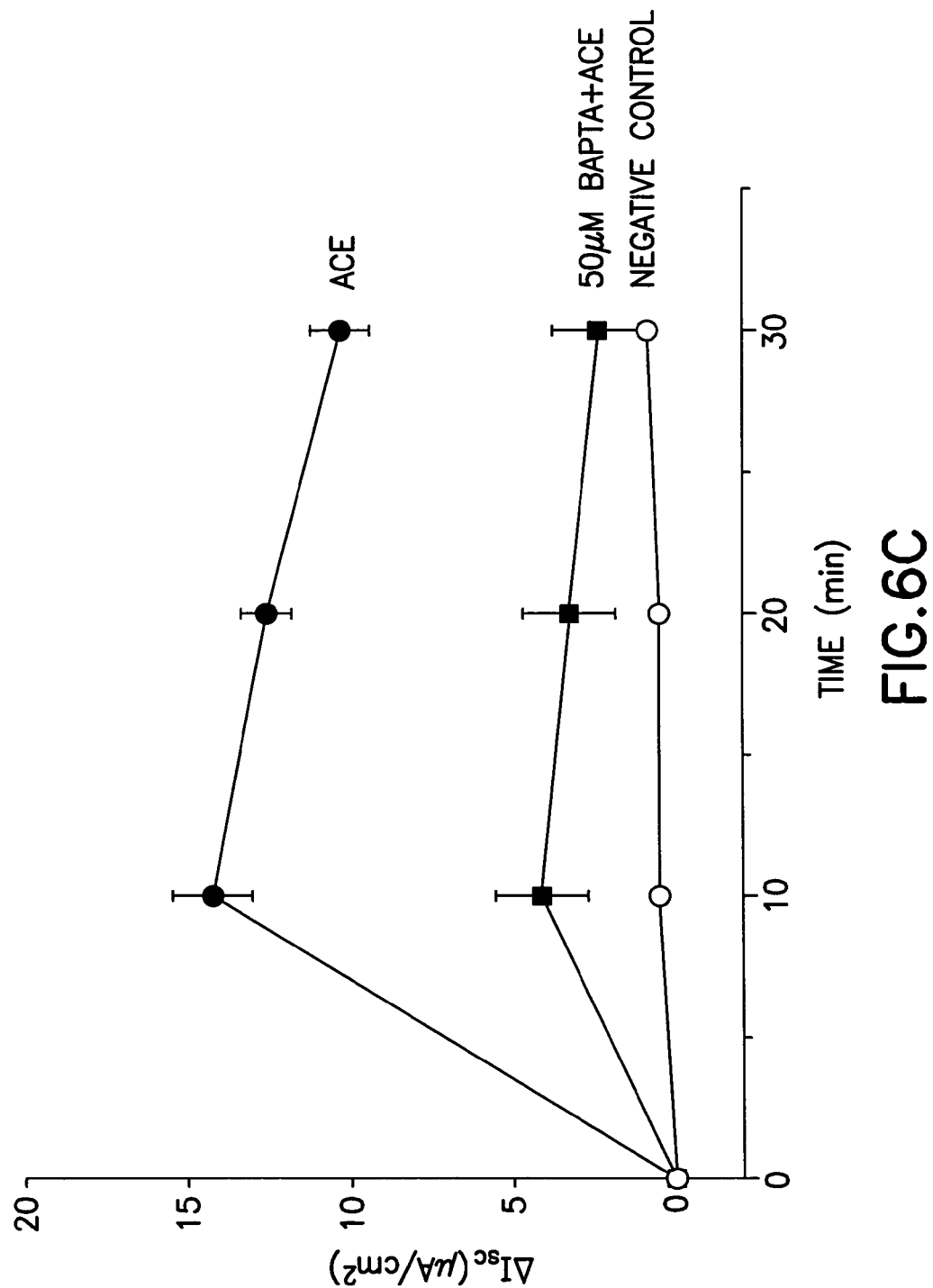
Figure 6D:
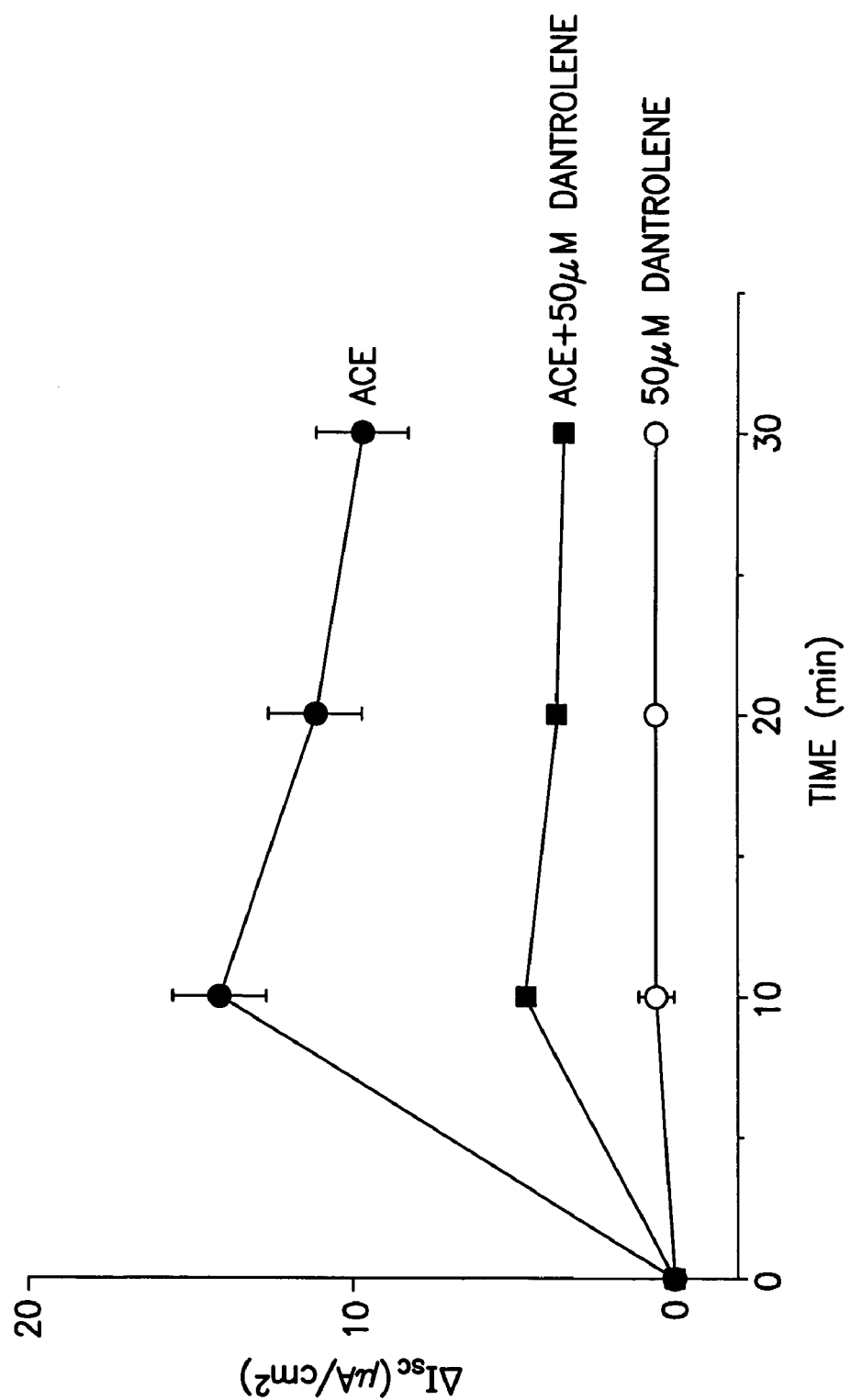

The intracellular calcium chelator, BAPTA, is employed to further confirm that the Ace effect is mediated by calcium. When T84 cell monolayers are preloaded with 50 μM BAPTA there is a near ablation of Ace-induced $I_{sc}$ without alteration of the monolayer's resistance (FIG. 6C, P<0.001, n=5). In FIG. 6C, BAPTA ("■") is added to the apical and basolateral baths 60 minutes prior to the addition of Ace ("●" is Ace alone; "O" is the negative control). As illustrated in FIG. 6D, pretreatment of T84 cell monolayers with dantrolene (50 μM; "■"), an intracellular calcium antagonist added to apical and basolateral baths 30 minutes prior to the addition of Ace, inhibits the Ace-induced $I_{sc}$ response by approximately 70% (n=4, P=0.002). (In FIG. 6D "●" is Ace alone; and "O" is dantrolene alone.)

Figure 6E:
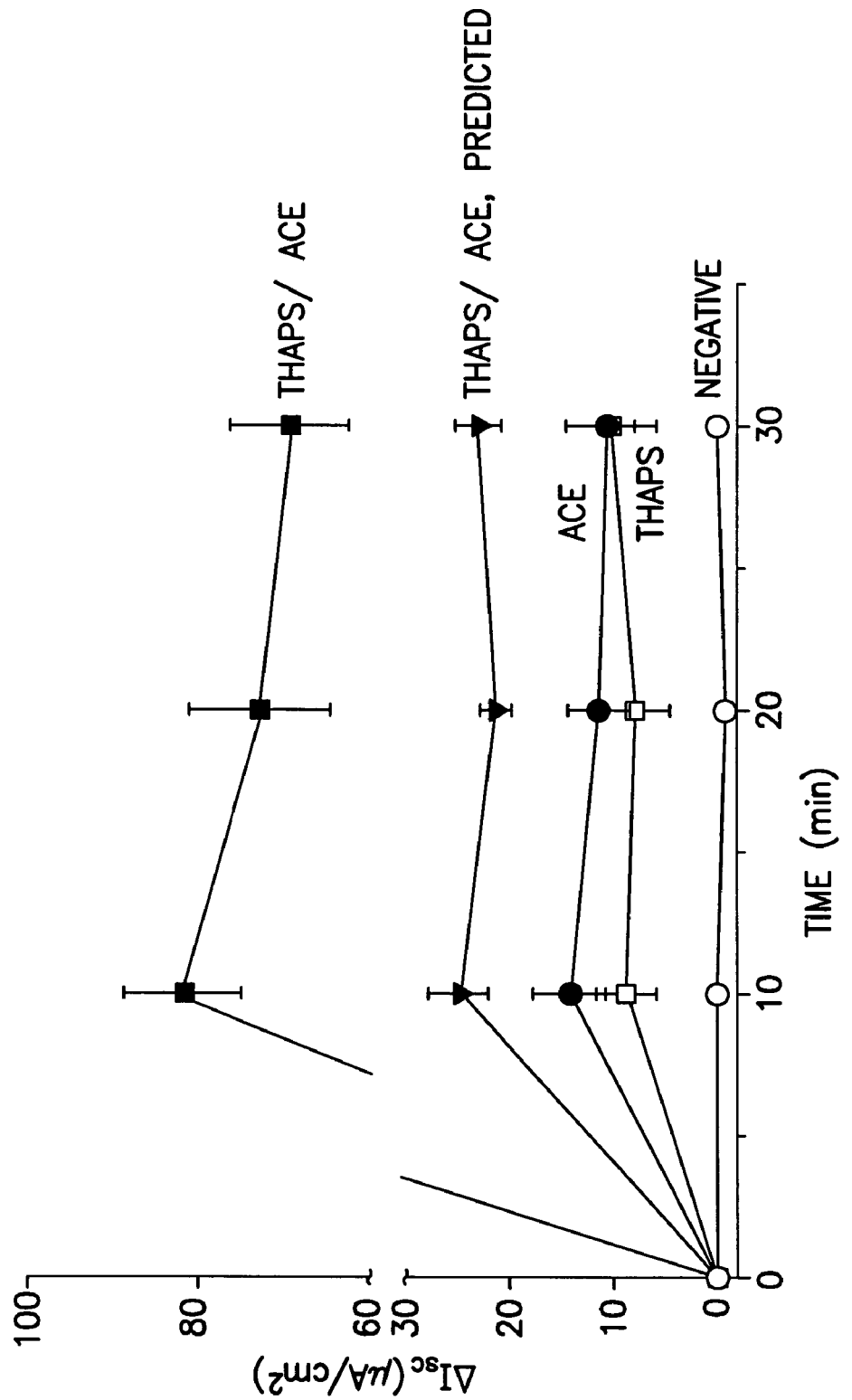

However, when T84 monolayers are pretreated at the basolateral side with thapsigargin (300 nM), a naturally occurring sesquiterpene lactone which induces a rapid increase in the concentration of cytosolic free $Ca^{2+}$ by direct discharge of intracellular stores (Thastrup et al., *Proc. Natl. Acad. Sci. USA* 87:2466-2470 (1990)), there is a potentiation of Ace-induced $I_{sc}$ (see FIG. 6E). In FIG. 6E thapsigargin alone (300 nM, "□") has a mean peak $I_{sc}$=10.2±4.3; Ace alone ("●") has a mean peak $I_{sc}$=14.0±3.5; thapsigargin followed by Ace 2 hours later ("■") has a mean peak $I_{sc}$=81.6±7.1; the predicted additive effect ("▼") has a mean peak $I_{sc}$=24.6±3.0 (P<0.001). Thapsigargin, which stimulates an increase in $I_{sc}$ and PD by discharging endoplasmic reticulum calcium stores (Uribe, J. M. et al., *Am.J.Physiol.* 271,1996.) potentiated Ace-stimulated $I_{sc}$ (n=5).

Together these results demonstrate that Ace's activity is dependent on both intra- and extracellular calcium and that Ace and thapsigargin act via different intracellular calcium pools.

Figure 7A:
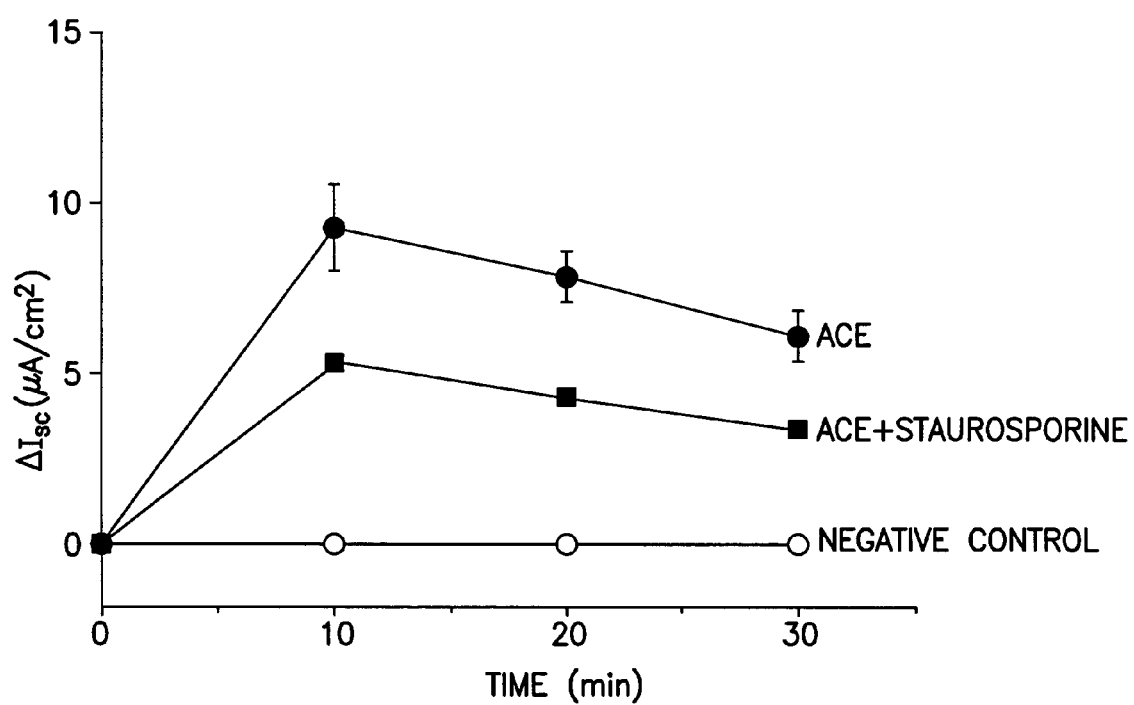
FIGS. 7A and 7B shows the effect of kinase inhibitors, staurosporine and genistein, on Ace-induced $I_{sc}$ response.
Figure 7B:
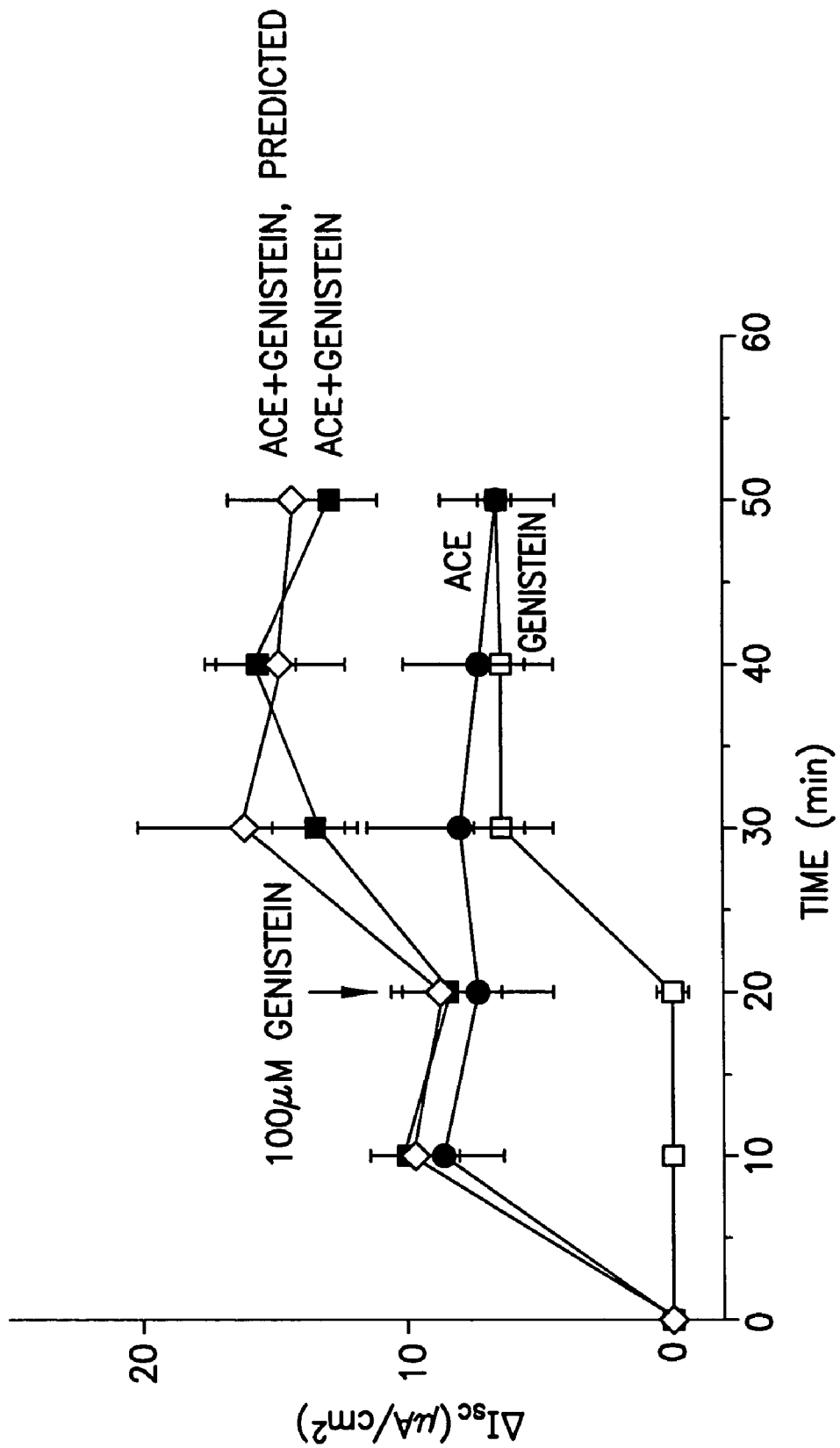
Figure 15:
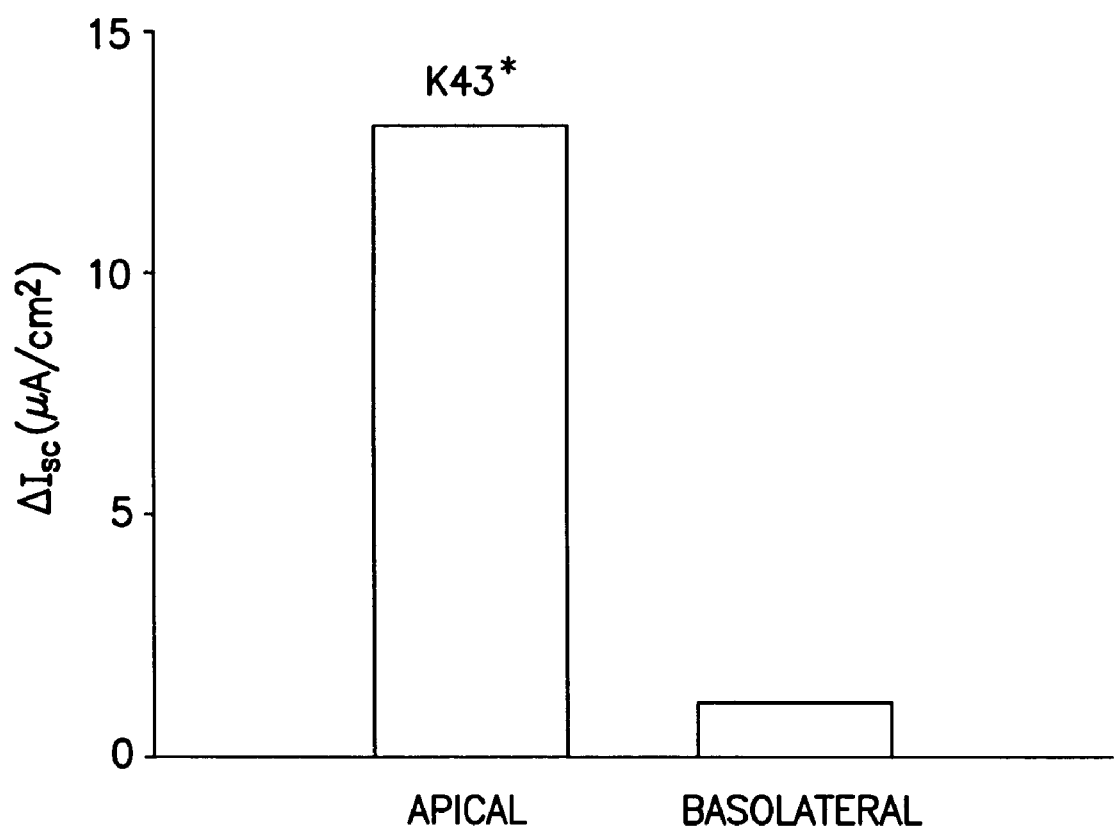
FIG. 15 shows that K43* has activity on the apical side, but not the basolateral side, of human bronchial epithelial cells.

To further examine the signaling pathways involved in the Ace-induced $I_{sc}$, the broad spectrum inhibitor of protein kinases, staurosporine, and the tyrosine kinase inhibitor, genistein, is utilized. As illustrated in FIG. 7A, 15 minute pretreatment with staurosporine (100 nM, "■") to the basolateral bath of T84 cell monolayer inhibits 45% of peak Ace-induced $I_{sc}$ (Ace alone is "●"; negative control is "O"; P=0.02, n=4). In contrast, in FIG. 7B, genistein (100 μM, "■") has no effect on the $I_{sc}$ response to Ace. In FIG. 7B, "●" is Ace alone, "□" is genistein (100 μM) alone added to basolateral bath of the T84 monolayer, and "◇" is the predicted additive effect (P=0.3, n=4).

Figure 8A:
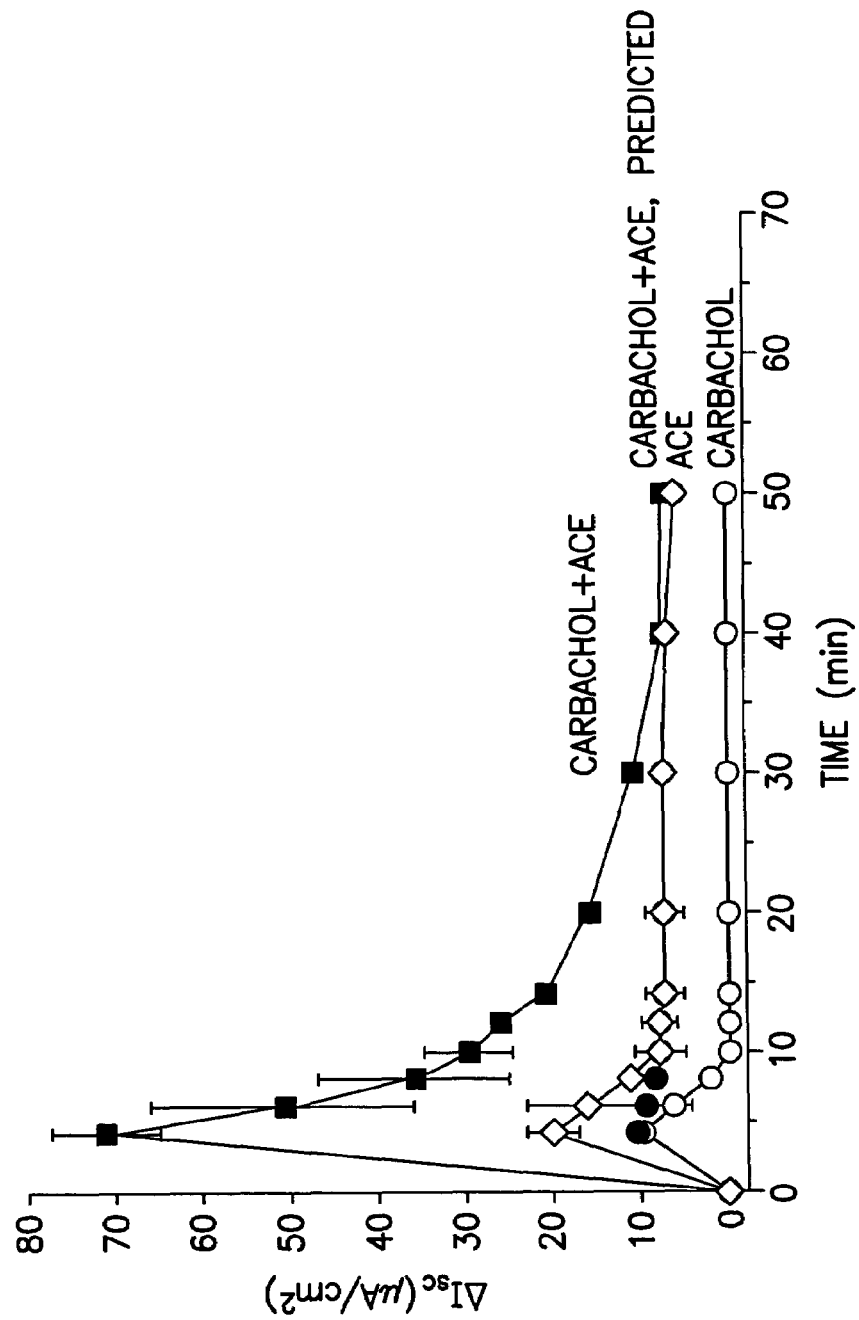
FIGS. 8A and 8B show the effect of Ace and carbachol alone or simultaneous and the effect of serial addition of both carbachol and Ace or carbachol and thapsigargin on T84 cell monolayers.

The $Cl^-$ secretory responses of T84 monolayers to Ace plus agonists acting via calcium (carbachol) or cyclic nucleotides (STa, forskolin). For these experiments, agonists are added at a concentration that stimulated a maximal $I_{sc}$ response when added individually ($10^{-4}$ M carbachol, $4.4×10^{-7}$ M STa, $1×10^{-5}$ M forskolin). Ace is utilized at a near-maximal concentration of $5×10^{-7}$ M. As previously reported (Dharmsathaphorn et al., (1986)), the $Cl^-$ secretory response of T84 cell monolayers to carbachol alone ("O"; added to the basolateral membrane) is rapid and transient, with a peak $I_{sc}$ of 9.8±1.1 μAmp/cm² at 4 minutes and a return nearly to baseline by 10 minutes (FIG. 8A). In contrast, Ace alone (" ") stimulates a rapid but persistent increase in $I_{sc}$ with a peak of 10.5±0.9 μAmp/cm² at 4 minutes (FIG. 8A). Simultaneous addition of Ace and carbachol (FIG. 8A, "■" is the combination and "◇" is the predicted additive effect) or serial addition of Ace then carbachol (data not shown) results in a synergistic response which is apparent by 4 minutes, with a peak $I_{sc}$ of 71.0±6.0 μAmp/cm² and which persists for at least 30 minutes (predicted additive effect, 20.0±1.3 μAmp/cm²; P<0.001; n=3).

Figure 8B:
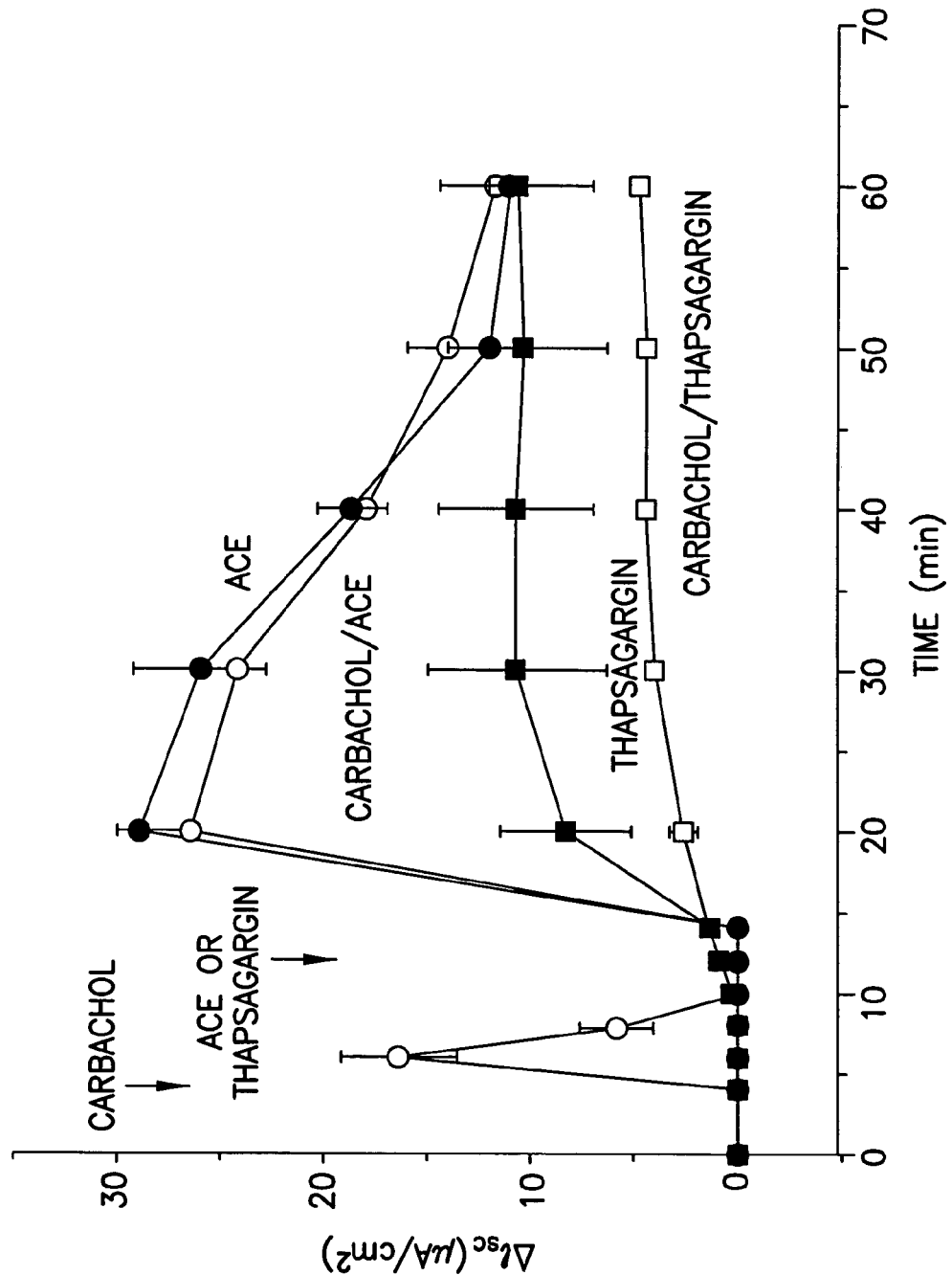

However, if carbachol is added prior to Ace (i.e., T84 cell monolayers are pretreated with carbachol ($10_{-4}$ M, basolateral membrane) 15 minutes prior to the addition of Ace), the Ace-induced chloride secretion is not augmented (FIG. 8B, "O" is carbachol pretreatment and "●" is Ace alone) nor blocked. Of note, pretreatment of T84 cell monolayers with carbachol ($10^{-4}$ M) 15 minutes prior to the addition of thapsigargin (1 μM) blocks thapsigargin-induced chloride secretion (the $I_{sc}$ response) as previously reported (FIG. 8B, "□" is carbachol followed by thapsigargin treatment and "■" is thapsigargin alone) (P<0.08, n=3) (Kachintorn et al., *Am. J. Physiol.* 264:C671-C676 (1993)). This data, combined with the data presented in FIG. 6, again demonstrate that the mechanism of Ace- and thapsigargin-induced $I_{sc}$ is through activation of different $Ca^{2+}$ pools.

In contrast, the $Cl^-$ secretory responses of T84 cell monolayers to *E. coli* STa or forskolin, cGMP and cAMP agonists respectively, are not enhanced by Ace. Simultaneous addition of Ace and STa or Ace and forskolin produces an additive response with a peak $I_{sc}$ of 32±3.8 μAmp/cm², predicted additive effect being 20.0±5.5 μAmp/cm² (Ace+STa, actual vs. predicted, P=0.14, n=3), and a peak $I_{sc}$ of 38.9±5.7 μAmp/cm², predicted additive effect being 54.3±6.8 μAmp/cm² (Ace+forskolin, actual vs. predicted, P=0.15, n=3). This lack of synergy between a $Ca^{2+}$ agonist (Ace) and cyclic nucleotide agonist (STa or forskolin) is unexpected, as calcium- and cyclic nucleotide-dependent agonists normally show synergy. Control experiments are performed examining the secretory responses of T84 monolayers to serial addition of *E. coli* STa followed by carbachol and response of monolayers to forskolin followed by carbachol. As expected, these agonists demonstrate the reported synergy of calcium- and cyclic nucleotide-dependent agonists (Levine et al., *Am. J. Physiol.* 261:G592-G601 (1991); Warhurst et al., *Cell Calcium* 15:162-174 (1994)) (STa followed by carbachol, mean peak $I_{sc}$=45.0 μAmps/cm² vs. predicted additive effect, mean peak $I_{sc}$=14.5±0.5, P<0.001, n=2; forskolin followed by carbachol, mean peak $I_{sc}$=69.3±2.4 μAmps/cm² vs. predicted additive effect, mean peak $I_{sc}$=49.0±2.9, P=0.005, n=3).

Figure 9:
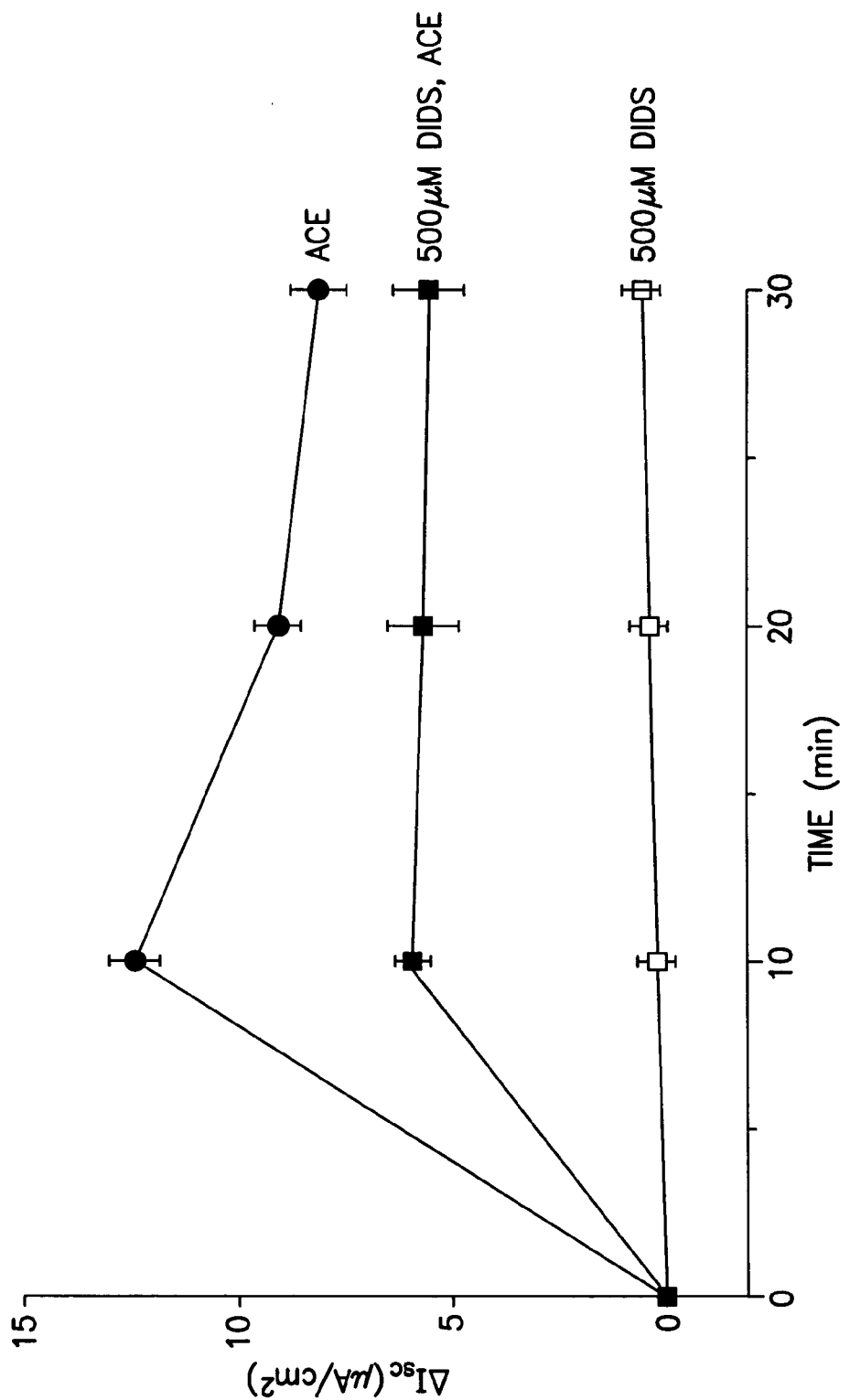
FIG. 9 shows the effect of DIDS alone or Ace with DIDS pretreatment on the $I_{sc}$ response by T84 cell monolayers.

Ace-stimulated $Cl^-/HCO_3^-$ secretion is partially dependent on a DIDS-sensitive apical chloride channel. The apical membrane of polarized T84 cells contains two distinct chloride channels, differentiated by their sensitivity to DIDS and anion selectivity (Merlin et al., *Am. J. Physiol.* 275:C484-C495 (1998)). The DIDS-insensitive channel that is activated by cAMP agonists presumably represents CFTR. Both cAMP and $Ca^{2+}$ agonists activate the DIDS-sensitive chloride channel. To determine which of the two channels is activated by Ace, T84 cell monolayers are treated with 500 μM DIDS on the apical membrane 30 minutes prior to Ace addition. DIDS-treated monolayers show a 50% inhibition of the Ace-induced $I_{sc}$ response (FIG. 9 where "●" is Ace alone; "□" is DIDS alone; and "■" is DIDS pretreatment followed by Ace) (P<0.001, n=7). This 50% reduction in activity is in contrast to 100% inhibition of thapsigargin-induced $I_{sc}$ response and 40% inhibition of forskolin-induced $I_{sc}$ response by DIDS reported previously (Merlin et al., (1998)).

Figure 10:
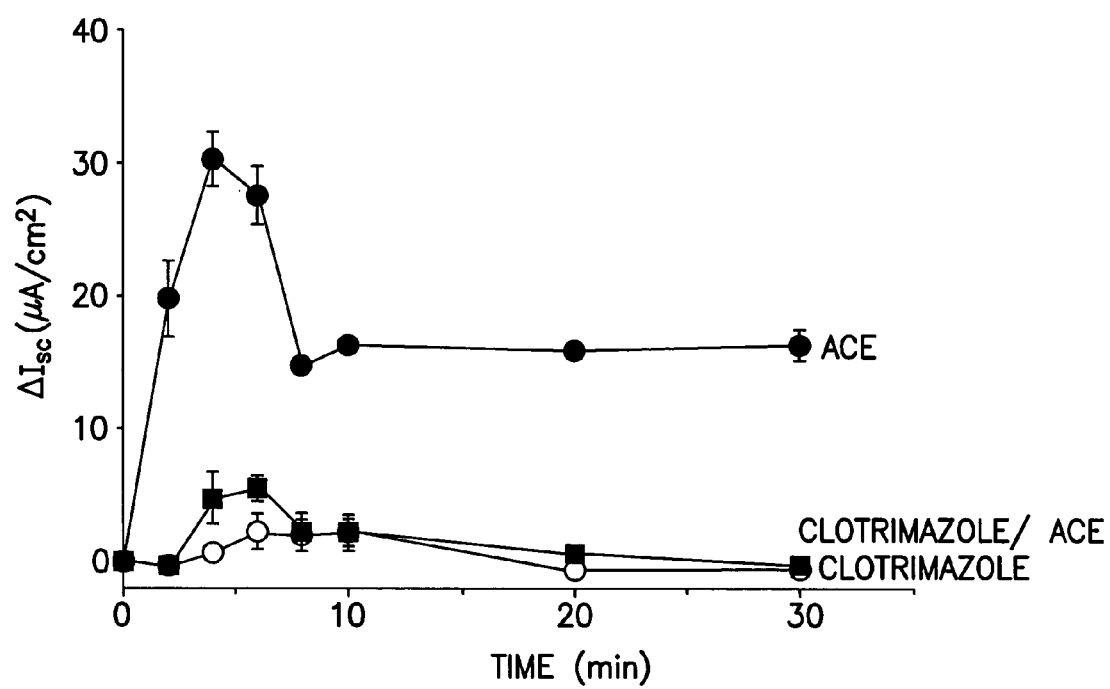
FIG. 10 shows the effect of clotrimazole pretreatment on the Ace-stimulated $I_{sc}$ response by T84 cell monolayers.

Ace-stimulated secretion is inhibited by clotrimazole. To ascertain the involvement of the basolateral membrane in Ace-stimulated secretion, the effects of clotrimazole on Ace-mediated $Cl^{31}/HCO_3^-$ secretion are evaluated. In previously reported studies, clotrimazole was identified as an inhibitor of both basolateral membrane $K^+$ channels, $K_{Ca}$ and $K_{cAMP}$ (Devor et al., *Am. J. Physiol.* 273:C531-C540 (1997)). Clotrimazole treated T84 cell monolayers show a 92% reduction in Ace-stimulated $I_{sc}$ as compared to control monolayers. As illustrated in FIG. 10, clotrimazole (30 µM) added to the T84 cell monolayer (apical and basolateral baths, Ringer's buffer) 30 minutes prior to Ace addition ("●" is Ace alone; "O" is clotrimazole alone; "●" is clotrimazole followed by Ace; P<0.001, n=4) virtually stops the activity of Ace. This clotrimazole inhibition of the Ace-stimulated $I_{sc}$ is similar to the 91% to 94% inhibition of cyclic nucleotide agonist-dependent chloride secretion by clotrimazole (Rufo et al., *J. Clin. Invest.* 100:3111-3120 (1997)) and the 84% inhibition of carbachol-dependent secretion (Rufo et al., *J. Clin. Invest.* 98:2066-2075 (1996)). These results demonstrate that Ace, like other cyclic nucleotide and $Ca^{2+}$-mediated agonists, depends on basolateral $K^+$ efflux pathways.

Thus, in T84 cell monolayers, Ace stimulates anion secretion which is dependent on the apical influx of extracellular calcium and select intracellular calcium pools. Furthermore, Ace exhibits a novel synergy with the acetylcholine analog, carbachol, but not with cyclic-nucleotide-dependent agonists, including the heat stable enterotoxin (STa) of *Escherichia coli* and forskolin.

Figure 11:
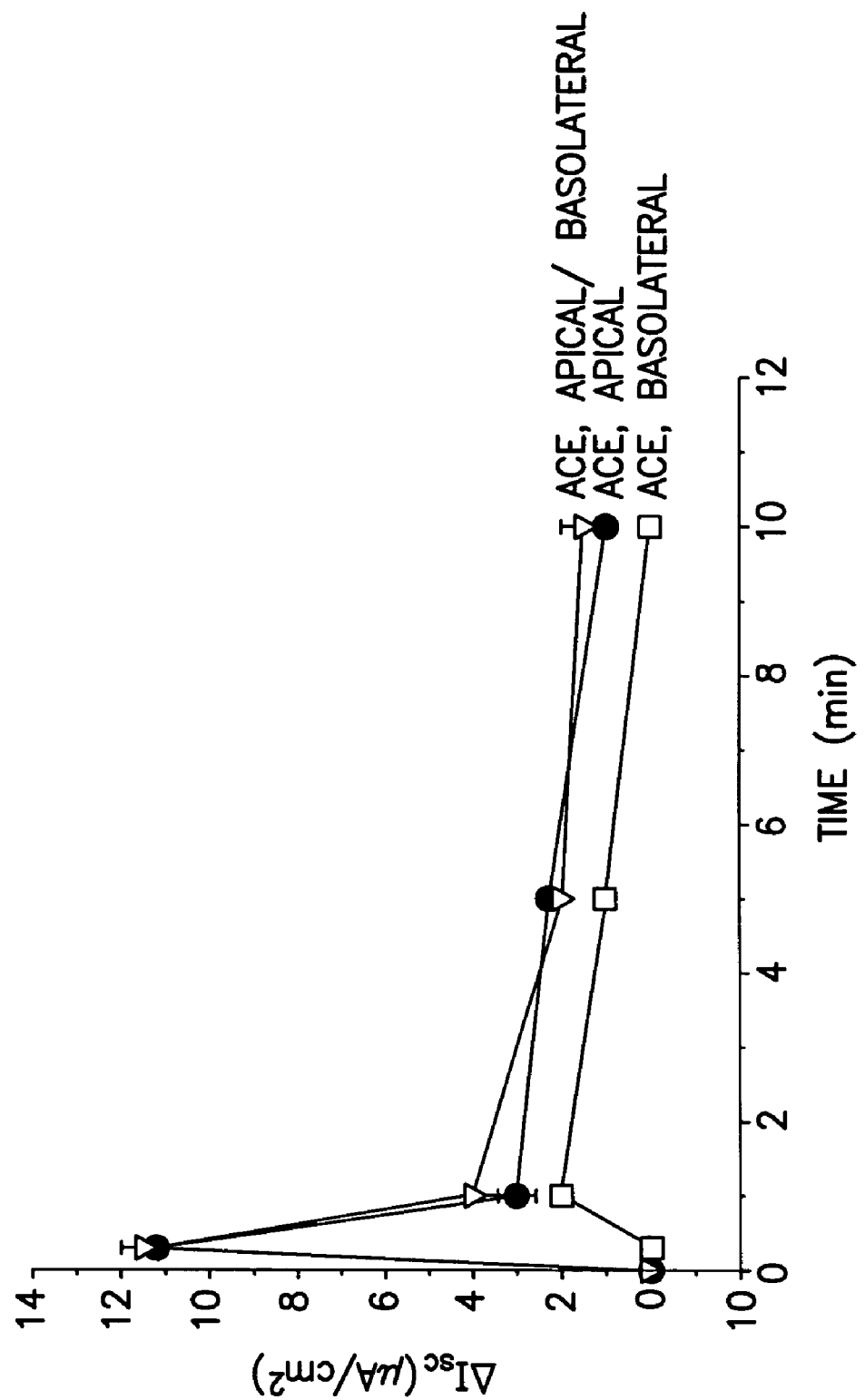
FIG. 11 shows the $\Delta I_{sc}$ in normal human bronchial cell line, 16HBE14o-, monolayers after being treated with Ace.
Figure 12:
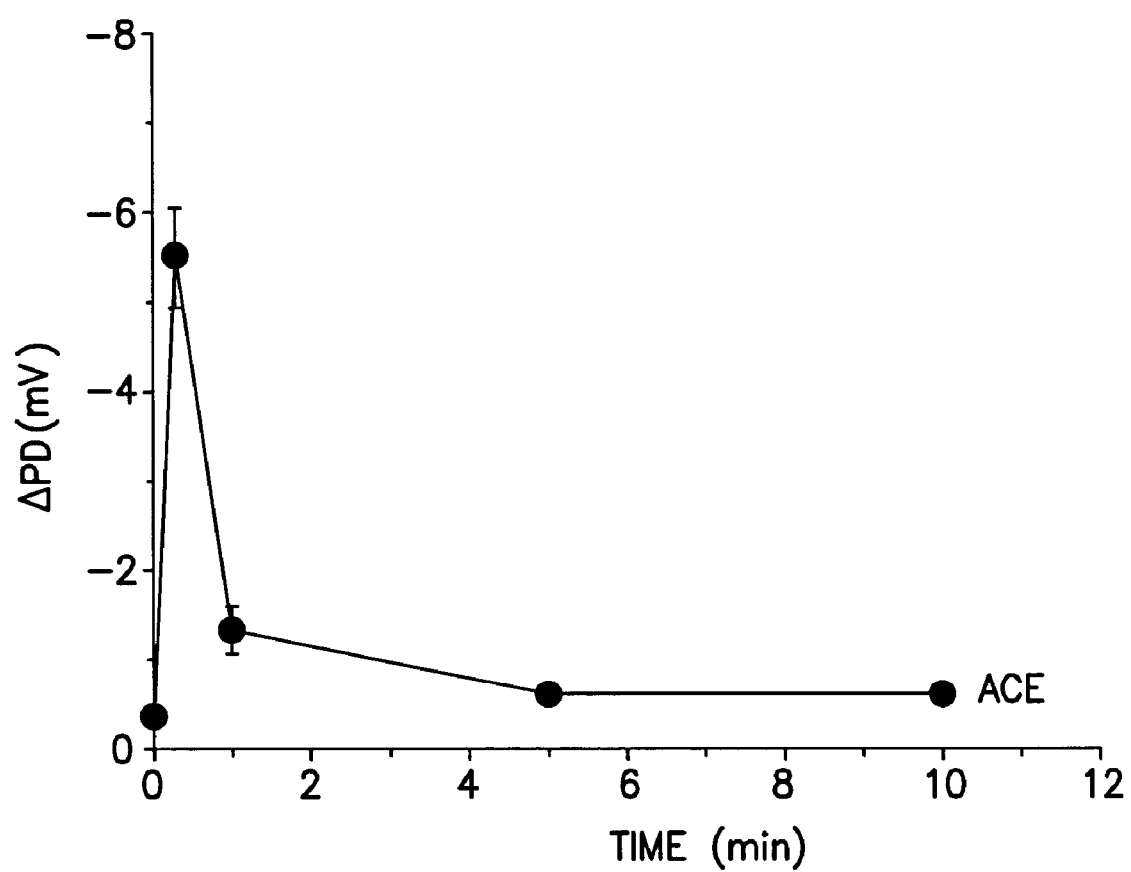
FIG. 12 illustrates the ΔPD in 16HBE14o- cell monolayers after being treated with Ace.

Ace activity in a normal human bronchial cell line, 16HBE14o-. To demonstrate that Ace stimulates $Cl^-/HCO_3^-$ secretion in normal human bronchial epithelial cells, the normal bronchial epithelial cell line, 16HBE14o- is used. The addition of ACE to the apical (" ") or apical plus basolateral ("∇") bathing solution of 16HBE14o- cell monolayers in modified Ussing chambers causes an increase in $I_{sc}$ (FIG. 11). Basolateral addition alone of Ace has no effect ("□", FIG. 11, peak $I_{sc}$, basolateral addition vs. apical addition, P<0.001). $I_{sc}$ reaches a maximal level of 11.3±0.3 µAmps/cm², 30 seconds after the addition of Ace to the apical bathing solution and then declines to baseline after 5 to 10 minutes. The addition of Ace to the apical bathing solution, also causes an increase in PD (FIG. 12), but results in no significant change in resistance.

Figure 13:
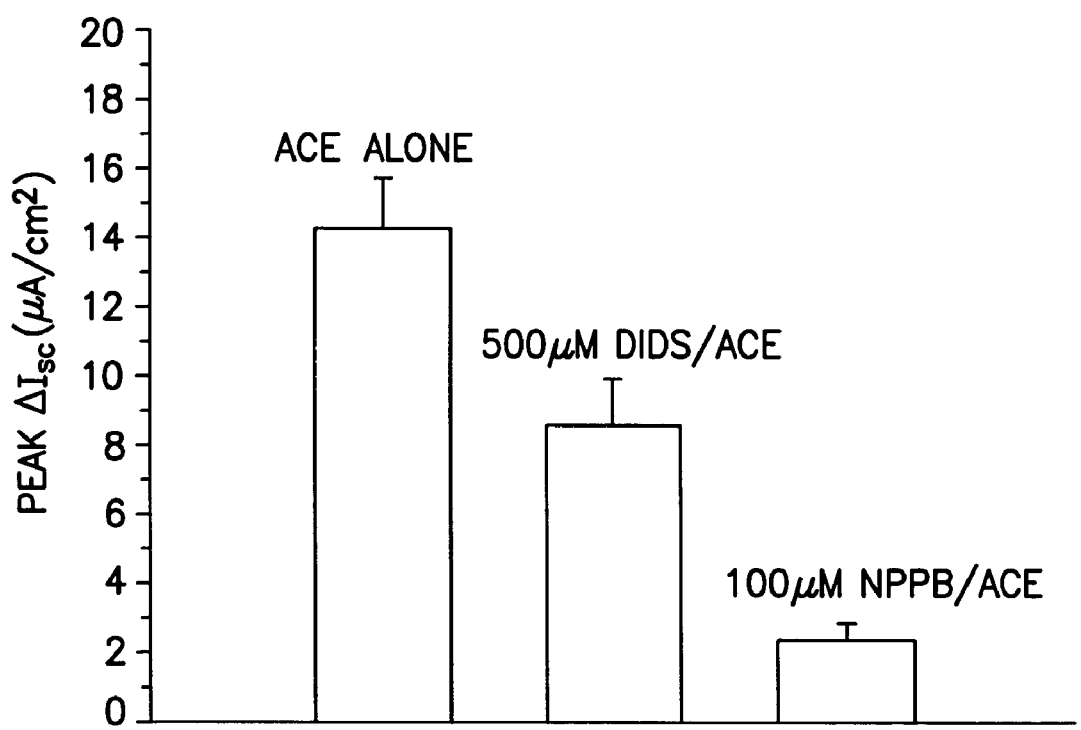
FIG. 13 illustrates the effects of DIDS and NPPB on Ace activity in 16HBE14o- cell monolayers.

ACE induced chloride secretion in T84 cell monolayers requires the activation of both apical chloride channels and basolateral transporters and $K^+$ channels (Trucksis, et al., *Am.J.Physiol. Cell Physiol.* 279: C567-C577). To determine whether ACE-stimulated $I_{sc}$ has similar requirements for both apical and basolateral channels and transporters in 16HBE14o- cell monolayers and which channels are required, inhibitor studies are performed. 16HBE14o- cell monolayers are pretreated with the anion channel blockers DIDS or NPPB (apical chloride channel inhibitors) or the basolateral $K^+$ channel inhibitor, clotrimazole. Pretreatment of 16HBE14o- cell monolayers with either DIDS (500 µM) or NPPB (100 µM) reduces ACE-stimulated $I_{sc}$. DIDS treated 16HBE14o- cell monolayers exhibit a 40% decrease in ACE-stimulated $I_{sc}$ (FIG. 13, Ace alone, mean peak $I_{sc}$=14.3±1.4; Ace addition following pretreatment of 16HBE14o- cell monolayers with DIDS, mean peak $I_{sc}$=8.5±1.3; P<0.03), while NPPB treated 16HBE14o- cell monolayers exhibit an ~80% decrease in ACE-stimulated $I_{sc}$ (FIG. 13, Ace addition following pretreatment of 16HBE14o- cell monolayers with NPPB, mean peak $I_{sc}$=2.3±0.5; P<0.001). The partial inhibition of Ace-induced secretion with either DIDS or NPPB confirms the expression of both CFTR and CaCC on the apical side of the 16HBE14o- cell monolayers and that Ace-induced current is dependent in part on both chloride channels.

Figure 14:
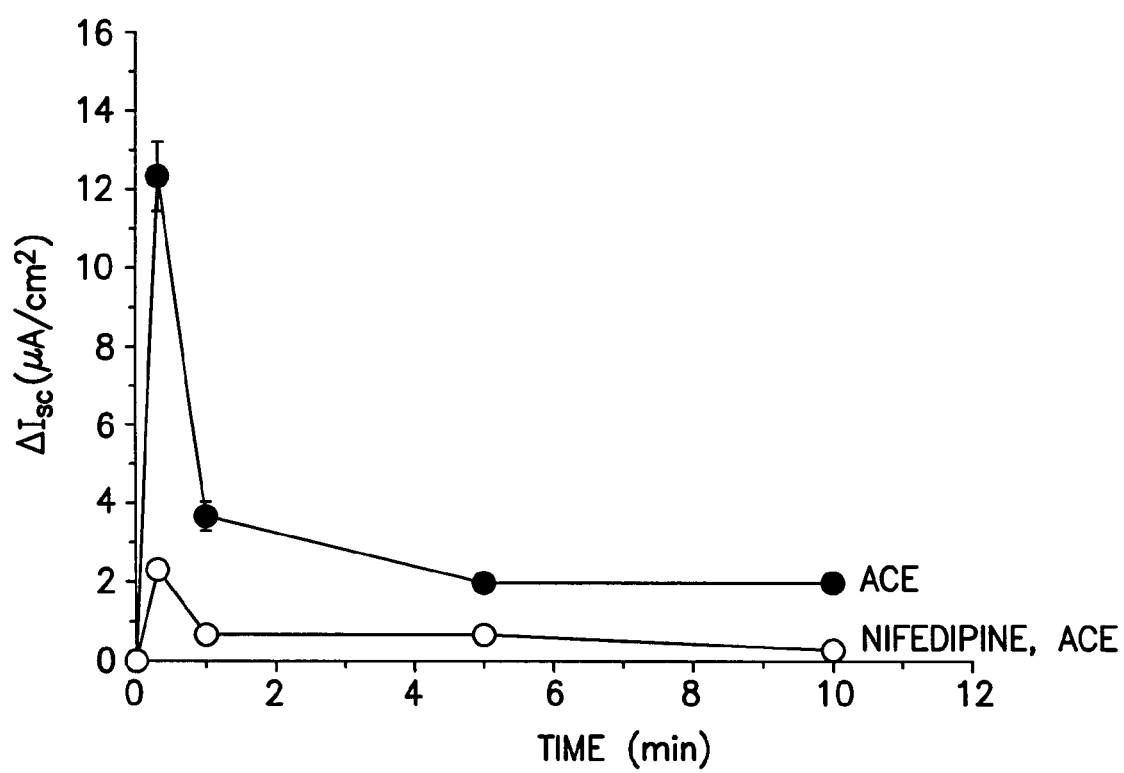
FIG. 14 illustrates the effect of nifedipine on Ace activity in 16HBE14o- cell monolayers.

Pretreatment of the 16HBE14o- cell monolayers with the $Ca^{2+}$ channel blocker nifedipine ("O") inhibits the Ace-induced $I_{sc}$ response as it did in T84 cells (FIG. 14, Ace alone "●", mean peak $I_{sc}$=12.3±0.9; Ace addition following pretreatment of 16HBE14o- cell monolayers with nifedipine, mean peak $I_{sc}$=2.3±0.3; P<0.001). This result confirms that in normal human bronchial epithelial cells the Ace-induced current is partially dependent on influx of $Ca^{2+}$.

Effectiveness of Ace in Cystic Fibrosis Cell Lines

To demonstrate that Ace induces chloride secretion in cystic fibrosis patients, experiments similar to the experiments described above for T84 cells and 16HBE14o- cells are performed using CFBE41o- cell monolayers. CFBE41o- cells are a human airway epithelial cell line having the CFTRΔF508 mutation, the most common mutation in CF patients. Because the expression of CaCC is upregulated (Fuller et al., *Clin Exp Pharmacol Physiol* 27:906-10, 2000) in the presence of a CF mutation, the DIDS sensitive Ace response is greater in the CFBE41o- cell monolayers than in 16HBE14o- cell monolayers which have the wild type CFTR gene.

Ace Analogs

The full-length wild-type Ace protein (having the amino acid sequence shown in FIG. 17, SEQ ID NO: 2), can be used to treat cystic fibrosis and other diseases involving defective chloride and/or bicarbonate secretion. However, it may be preferable for one to use an Ace analog instead of Ace. An Ace analog is a polypeptide variant, mutant, homolog, or fragment of Ace that binds to and activates the CaCC. In one embodiment, an Ace analog is a polypeptide having at least 85% homology, more preferably at least 90% homology, to wild-type Ace. In this embodiment, an Ace analog can have amino acid substitutions (preferably between one and five amino acid substitutions) which result in an increase, decrease or no change of functional activity compared to wild-type Ace. In another embodiment an Ace analog is a polypeptide which has deletions of amino acids compared to wild-type Ace. Deletions can be internal, at the carboxyl terminal, at the amino terminal, or a combination of these. Examples of Ace analogs are as follows (Table 1):

| Name | Type of Mutation |
|---|---|
| L74* | truncation, leucine changed to stop codon (FIG. 18, SEQ ID NO: 3) |
| I58* | truncation, isoleucine changed to stop codon (FIG. 19, SEQ ID NO: 4) |
| K43* | truncation, lysine changed to stop codon (FIG. 20, SEQ ID NO: 5) |
| Q35* | truncation, glutamic acid changed to stop codon (FIG. 21, SEQ ID NO: 6) |
| K43A | substitution, lysine changed to alanine (FIG. 22, SEQ ID NO: 7) |
| K21A | substitution, lysine changed to alanine (FIG. 23, SEQ ID NO: 8) |
| K30A | substitution, lysine changed to alanine (FIG. 24, SEQ ID NO: 9) |
| E28A | substitution, glutamic acid changed to alanine (FIG. 25, SEQ ID NO: 10) |
| E39A | substitution, glutamic acid changed to alanine (FIG. 26, SEQ ID NO: 11) |
| M1A | substitution, methionine changed to alanine (FIG. 27, SEQ ID NO: 12) |
| M3A | substitution, methionine changed to alanine (FIG. 28, SEQ ID NO: 13) |
| M4A | substitution, methionine changed to alanine (FIG. 29, SEQ ID NO: 14) |

-continued

| Name | Type of Mutation |
|---|---|
| K43D5 | internal deletion of amino acids 41-45 (FIG. 30, SEQ ID NO: 15) |
| D11 | internal deletion of amino acids 35-45 (FIG. 31, SEQ ID NO: 16) |
| MT1 | combination of K43* and K21A (FIG. 32, SEQ ID NO: 17) |
| MT2 | combination of K43* and E28A (FIG. 33, SEQ ID NO: 18) |
| MT3 | combination of K43*, K21A, and E28A (FIG. 34, SEQ ID NO: 19) |

Ace analogs can be generated by site-directed mutagenesis (by using, for example, the QuickChange site-directed mutagenesis kit, Stratagene, Inc., La Jolla, Calif. (see below)) or produced as a synthetic polypeptide (for example by Bio-Synthesis, Inc., Lewisville, Tex.) using well-known in the art techniques.

Ace and Ace analogs can be expressed in the methylotrophic yeast *Pichia pastoris* (Trucksis, et al., *Infect. Immun.* 65:4984-4988, 1997). This system has successfully been used to express and purify a variety of heterologous proteins including an active enzyme (Hagenson, et al., *Enzyme Microb. Technol.* 11:650-656, 1989) and hydrophobic membrane proteins (Despreaux, et al., *Gene* 131:35-41, 1993). Alternatively, one can isolate Ace and/or Ace analogs from *V. cholerae*. Expression vectors having DNA which encode for an Ace analog or full-length Ace can be used for expression in bacteria (Galen, Plasmid Maintenance System for Antigen Delivery; International Patent Application PCT/US99/28499 published on Jun. 8, 2000 as WO 00/32047). Other types of expression vectors for prokaryotes and eukaryotes are well-known in the art field. Suitable expression vectors include, but are not limited to, retroviral vectors, vaccinia viral vectors, CMV viral vectors, BLUESCRIPT (Stratagene, La Jolla, Calif.), bacculovirus vectors, and pBR322 for *E. coli* (Bolivar, et. al., *Gene,* 2:95, 1977). The expression vectors contain the DNA sequence of an Ace analog or Ace downstream of an inducible or constitutively expressed promoter and enhancer. Examples of suitable regulatory sequences for use in various prokaryotic and eukaryotic cells are well-known (see Ausubel, et. al., *Short Protocols in Molecular Biology,* 3rd ed., John Wiley & Sons, Inc., New York, 1997).

If one expresses Ace or an Ace analog in prokaryotic cells and/or eukaryotic cells, then one would need to purify Ace or the Ace analog. Purification can include the following steps: (1) solubilization of the desired protein, (2) the development of one or more isolation and concentration procedures, (3) stabilization of the protein following purification, and (4) development of a suitable assay to determine the presence of the desired protein. Various aspects of protein isolation and purification are discussed in detail in Cooper, T. G., "The Tools of Biochemistry," John Wiley & Sons, New York, 1977. As the techniques of protein isolation and purification are notoriously well known in the art, this disclosure will refrain from discussing them in detail. Nevertheless, elements of the cited reference are summarized and discussed below.

Solubilization is required of most proteins to be purified, as most isolation procedures commonly used operate in aqueous solutions. In some cases solubilization can be achieved by merely lysing a host cell within which a desired protein has been expressed. In other situations, additional steps, such as extracting the desired protein from a subcellular organelle may be required. Osmotic lysis, grinding, the use of blenders, ultrasonic waves, presses, and other well known techniques of protein solubilization are contemplated for use with the methods disclosed herein.

Regarding the isolation and concentration of Ace or Ace analogs, there are variety of techniques available that are well known in the art. These techniques include (1) differential solubility, (2) ion exchange chromatography, (3) absorption chromatography, (4) molecular sieve techniques, (5) affinity chromatography, (6) electrophoresis, and (7) electrofocusing. Each of these techniques can be useful in the purification of Ace or Ace analogs.

Stabilizing and maintaining a purified Ace or Ace analog in a functional state warrants attention to a number of different conditions. These conditions include (1) pH, (2) degree of oxidation, (3) heavy metal concentration, (4) medium polarity, (5) protease concentration, and (6) temperature. One of ordinary skill in the art would readily know which of the available techniques to use to maintain purified Ace or Ace analogs in an active form without undue experimentation.

Various Ace analogs are tested on monolayers of T84 cells, 16HBE14o- cells, and CFBE14o- cells to determine the activity and efficiency of the Ace analogs. The activity of various Ace analogs on T84 cells in modified Ussing chambers is presented in the table below.

TABLE 2

| Strain | Mutation Description | $\Delta I_{sc}$ ($\mu A/cm^2$)[a] | P value | Relative activity (%)[b] |
|---|---|---|---|---|
| CVD113 (pCVD630) | wild-type | 25.3 ± 2.1 [12] | | 100 |
| Class I mutants: | Carboxyl terminal deletions, alpha helical wheel deleted | | | |
| L74* | Leucine → Stop codon | 15.8 ± 1.9 [4] | 0.02[c] | 50 |
| I58* | Isoleucine → Stop codon | 19.3 ± 1.3 [4] | 0.11 | 78 |
| K43* | Lysine → Stop codon | 29.8 ± 1.9 [4] | 0.24 | 119 |
| Q35* | Glutamine → Stop codon | 11.0 ± 1.4 [4] | 0.001[c] | 48 |
| Class II mutants: | Charged AA to alanine | | | |
| K43A | Lysine → alanine | 14.1 ± 1.9 [7] | 0.001[c] | 66 |
| K21A | Lysine → alanine | 26.3 ± 0.6 [4] | 0.80 | 103 |
| K30A | Lysine → alanine | 7.8 ± 1.0 [5] | <0.001[c] | 35 |
| E28A | Glutamic acid → alanine | 34.2 ± 4.1 [6] | 0.04[d] | 114 |
| E39A | Glutamic acid → alanine | 31.3 ± 2.1 [4] | 0.13 | 83 |

TABLE 2-continued

| | | $\Delta I_{sc}$ (µA/cm$^2$)$^a$ | P value | Relative activity (%)$^b$ |
|---|---|---|---|---|
| Class III mutants | Initial methionine to alanine | | | |
| M1A | Methionine → alanine | 18.5 ± 0.9 [4] | 0.07 | 72 |
| M3A | Methionine → alanine | 5.7 ± 0.8 [6] | <0.001$^c$ | 19 |
| M4A | Methionine → alanine | 11.6 ± 1.6 [5] | <0.001$^c$ | 51 |
| Class IV mutants | Internal non-polar deletion | | | |
| K43D5 | Deletion of AA's 41-45 | 13.0 ± 1.3 [5] | 0.002$^c$ | 60 |
| D11 | Deletion of AA's 35-45 | 4.8 ± 0.5 [6] | <0.001$^c$ | 16 |

$^a$Results are the means $\Delta I_{sc}$ ± S.E.M. Number of experiments are as indicated in brackets.
$^b$Activities are expressed as the area under the curve ($\Delta I_{sc}$ vs. time) relative to wild-type Ace (pCVD630) which was normalized to 100%.
$^c$Wild-type Ace vs. Ace analog peak $\Delta I_{sc}$, significant P values indicating Ace analog has significantly less secretory activity.
$^d$Wild-type Ace vs. Ace analog peak $\Delta I_{sc}$, significant P values indicating Ace analog has significantly greater secretory activity.

To determine structure-activity relationships in the Ace toxin, site-directed mutagenesis is used to construct Ace analogs. Mutations are engineered into the ace gene encoded on plasmid pCVD630 using the QUIKCHANGE™ site-directed mutagenesis kit (Stratagene, Inc.) per manufacturer's instructions. The reaction utilizes a double-stranded DNA template (pCVD630) and two synthetic complementary oligonucleotide primers containing the desired mutation with extension from the primers during temperature cycling by using PfuTurboT DNA polymerase. Incorporation of the oligonucleotide primers generates a mutated plasmid containing staggered nicks. Following the thermal reaction, the product is treated with DpnI endonuclease to digest the methylated and hemimethylated parent DNA template. The remaining nicked vector DNA containing the desired mutation is transformed into supercompetent cells. Plasmid DNA is purified with QIAGEN™ columns (Qiagen Inc., Valencia, Calif.). Double-stranded sequencing of plasmid DNA to confirm sequence is performed at the Biopolymer Laboratory of the University of Maryland, Baltimore (Baltimore, Md.).

The plasmids identified to encode the desired Ace analogs are introduced into the *V. cholerae* Ace⁻ strain (CVD113⁻, CT⁻, Zot⁻, Ace⁻) by electroporation. CVD113 is grown in 100 ml L broth to an $OD_{600}$ of 0.6. The cells are made electrocompetent by washing three times with 0.137 M sucrose solution, and finally resuspending in 0.5 ml of the sucrose solution. Two to 5 µl of plasmid DNA containing the sequence which encodes for an Ace analog are added to 200 µl of electrocompetent CVD113 cells and transformed with a Gene Pulser II (Bio-Rad Laboratories, Hercules, Calif.) using parameters of 2.5 kV, 400 Ω, and 25 µF. The Ace analogs are partially purified from culture supernatants of *V. cholerae* to obtain a 5,000-30,000 $M_r$ fraction and analyzed on monolayers in Ussing chambers for the ability to induce a change in short-circuit current ($\Delta I_{sc}$).

K43*, a nonsense mutation which eliminated the carboxyl terminal half of the Ace protein (FIG. 20, SEQ ID NO: 5), retains full activity in T84 cell monolayers (see Table 2). This finding indicates that the helical wheel confirmation present at the carboxyl-terminus of the Ace protein (and which is deleted in K43 *) is not required for the Ace-stimulated $I_{sc}$ response in T84 monolayers. K43* is at most 42 amino acids in length (depending on the initiating methionine).

K43*, when added to the apical side of 16HBE14o- cell monolayers, causes a current of approximately 13 $\mu A/cm^2$ (FIG. 15). Similar to the full length Ace protein, K43*, when added to the basolateral side of the 16HBE14o- cell monolayers, generates almost no current.

Two other Ace analogs having amino acid substitutions, K2IA and E28A, retained full activity on T84 cell monolayers (see Table 2). K21A (FIG. 23, SEQ ID NO: 8) has a lysine changed to an alanine. E28A (FIG. 25, SEQ ID NO: 10) has a glutamic acid changed to alanine.

A thirty-five amino acid Ace analog (Q35*) had approximately one-half the activity on T84 cell monolayers of wild-type Ace, indicating that the amino acids between position 35 and 43 play an important role in Ace secretory activity. Interestingly, Ace analogs longer than 43 amino acids had reduced activity on T84 cell monolayers compared to wild-type Ace (I58* had approximately 78% activity and L74* had approximately 50% activity). An Ace analog having a deletion of five amino acids from position 41-45 (K43D5, FIG. 30, SEQ ID NO: 15) had about two-thirds the activity of wild-type Ace on T84 cell monolayers. Furthermore, an Ace analog with a deletion of eleven amino acids from position 35-45 (D11, FIG. 31, SEQ ID NO: 16) had approximately 16% the activity of wild-type Ace on T84 cell monolayers. (See Table 2.)

It may be preferable to use K43 * to treat animals, including humans, having a disease involving abnormal chloride or bicarbonate transport because K43* retains full activity yet is small enough to be made synthetically. Alternatively, other Ace analogs may also be used to treat patients, such as MT1 (FIG. 32, SEQ ID NO: 17), MT2 (FIG. 33, SEQ ID NO: 18), or MT3 (FIG. 34, SEQ ID NO: 19). Other Ace analogs which may be useful to treat animals, including humans, may have deletions of amino acids from the amino terminal of K43*, thus reducing the size of the polypeptide that needs to be generated.

Ace and Ace Analogs for Treatment of Cystic Fibrosis

Ace or Ace analogs are administered to cystic fibrosis patients by inhalation, for example by using a meter dosage unit device, a nebulizer or nasal sprayer. The amount of Ace or Ace analog administered is sufficient to increase lung surface airway water by stimulation of the CaCC. The dose response curve of purified Ace protein (Trucksis, et al., *Am.J.Physiol. Cell Physiol.* 279:C567-C577, 2000) indicates that the threshold concentration of Ace that induced a significant increase in $I_{sc}$ on T84 monolayers is 36 nM, which corresponds to 200 ng of protein. It is understood that the dosage of Ace or Ace analog will vary, depending on the severity of the disease and the patient's bronchial surface area (which can itself depend on the patient's age and weight). It may be preferred that the actual dosage in patients be determined by assessing pulmonary function with spirometric measurements (Knowles, et al., *N.Engl.J.Med.* 322:1189-1194, 1990) and determining human nasal PD measurements (Knowles et al., *N.Engl. J.Med.* 325:533-538, 1991 and Singh et al. *J Pharmacol Exp Ther.* 292:778-87, 2000) after administration of Ace or an Ace analog by nasal spray. While customizing the dosage for each patient may be preferable, it is anticipated that the dosage of Ace or an Ace analog administered should be such that amount of Ace or Ace analog delivered to the bronchial surface with each dose administered range between 0.02 µg and 10 mg of polypeptide per $cm^2$ of bronchial surface area, more preferably between 0.2 µg and 500 µg of polypeptide per $cm^2$ of bronchial surface area, and most preferably range between 0.5 µg and 10 µg of polypeptide per $cm^2$ of bronchial surface area. (While it is anticipated that cystic fibrosis patients are human, it is understood that one may want to administer Ace or Ace analogs to animals, including mammals having cystic fibrosis like diseases or other diseases involving abnormal transport of chloride ions or bicarbonate ions.)

Inhaled or insufflated Ace and Ace analogues activate the CaCC, thus causing an increase in the level of chloride secretion by bronchial epithelial cells. With this increased chloride secretion, the cystic fibrosis patient will have increased airway surface water because of the movement of water along with the secretion of chloride. Because of the increased airway surface water, the cystic fibrosis patient who is taking Ace or an Ace analog will not suffer the deleterious effects of desiccation of the pulmonary tract such as a reduction in the activity of the bronchial ciliary, reduced mucociliary clearance, and an increase in bronchiolar plugging. Further, with an increase in airway surface water over the levels found in untreated cystic fibrosis patients, the Ace-treated or Ace analog treated cystic fibrosis patient has an increase in mucociliary clearance and reduced bronchiolar plugging compared to untreated cystic fibrosis patients. Ace or Ace analog-treated patients have fewer pulmonary infections and improved pulmonary function compared to untreated cystic fibrosis patients. With fewer pulmonary infections, the Ace treated or Ace analog treated cystic fibrosis patient will have reduced amounts of damage caused by neutrophil elastase compared to non-treated cystic fibrosis patients.

Other Chloride Secretion Deficiency Diseases

Chloride channels form a large functional family with structurally diverse members and are found in a variety of tissues. In cystic fibrosis there is impaired chloride permeability because of a defect in the cAMP-regulated chloride channel, CFTR. Other human diseases have also been found to result from mutations in chloride channels including Dent's disease (an inherited syndrome of nephrocalcinosis, rickets and end-stage renal failure), X-linked nephrolithiasis, X-linked recessive hypophosphatemic rickets, autosomal dominant myotonia congenita and autosomal recessive general myotonia. In these diseases the mutations in CFTR result in a decrease in chloride secretion compared to individuals without the disease and mutation. Ace or Ace analogs can be used to increase chloride secretion in individuals with these diseases by activation of the calcium dependent chloride channel (CaCC). The dosage of Ace or Ace analog that is to be administered to patients to increase chloride secretion will vary depending on the severity of the disease, the location of the site to be treated, the mode of administration, and the patient's age and weight. It is anticipated that the dosage of Ace or Ace analog administered should be such that the amount of Ace or Ace analog delivered to the site to be treated should range between 0.02 μg and 10 mg of polypeptide per $cm^2$ of surface area, more preferably between 0.2 μg and 500 μg of polypeptide per $cm^2$ of surface area, and most preferably range between 0.5 μg and 10 μg of polypeptide per $cm^2$ of surface area. Of course, the actual amount of Ace or Ace analog administered will vary in order to achieve the desired concentration of the polypeptide at the desired site of action.

Animals, including mammals, may suffer from similar diseases, diseases which are characterized by the reduction of chloride ion secretion or bicarbonate ion secretion from cells. For animals suffering from such conditions, one could alleviate the symptoms of the disease by administering Ace or an Ace analog to increase the amount of chloride secretion or bicarbonate secretion from cells by activating the CaCC.

Routes of Administration

Ace and Ace analogs can be administered by nasal or oral inhalation, oral ingestion, injection (intramuscular, intravenous, and intraperitoneal), transdermally, or other forms of administration. Inhalation is the preferred method for cystic fibrosis patients. For other diseases, other modes of administration may be preferable.

The inhalant form of Ace or Ace analog or intrabronchial route of administration of Ace or Ace analog may comprise liquid or powder compositions containing Ace or Ace analog and suitable for nebulization and intrabronchial use, or aerosol compositions administered via an aerosol unit dispensing metered doses (oral or nasal administration).

Suitable liquid compositions comprise for example, Ace or Ace analog in an aqueous, pharmaceutically acceptable inhalant solvent, e.g., isotonic saline or bacteriostatic water. The solutions are administered by a pump or squeeze-actuated nebulized spray dispenser, or by any other similar device for causing or enabling the requisite dosage amount of the liquid composition to be inhaled into the patient's lungs.

Suitable powder compositions include, by way of illustration, powdered preparations of Ace or Ace analog thoroughly intermixed with lactose or other inert powders acceptable for intrabronchial administration. The powder compositions can be administered via an aerosol dispenser or encased in a breakable capsule which may be inserted by the patient into a device that punctures the capsule and blows the powder out in a steady stream suitable for inhalation.

Aerosol formulations for use in this invention typically include fluorinated alkane propellants, surfactants and co-solvents and may be filled into aluminum or other conventional aerosol containers which are then closed by a suitable metering valve and pressurized with propellant, producing a metered dose inhaler.

As those skilled in the pharmaceutical arts will appreciate, many conventional methods and apparatus are available for administering precisely metered doses of intrabronchial medication and for regulating the desired dosage amount in accordance with patient weight and the severity of the patient's condition. Moreover, there are many art-recognized liquid, powder and aerosol vehicles suitable for the intrabronchial administration of Ace or Ace analogs, and many pharmaceutically acceptable oral and parenteral vehicles which may be employed for the oral and parenteral administration of Ace or Ace analogs. The invention is not limited to any particular inert vehicles, solvents, carriers, excipients or dosage forms and is not restricted to any particular methods or apparatus of intrabronchial administration.

For conditions other than cystic fibrosis, it may be appropriate to administer Ace or Ace analog as a liquid, solid, tablet, pill, lotion, microsphere encapsulation, and other known composition in the art field.

Ace or Ace analog can also be converted into a pharmaceutically acceptable salt or pharmaceutically acceptable solvate or other physical forms (e.g., polymorphs by way of example only and not limitation) via known in the art field methods. Pharmaceutically acceptable carriers can be used along with Ace or Ace analog. In making the compositions of the present invention, Ace or Ace analog can be mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier, or medium for Ace or Ace analog. Thus, the compositions can be in the form of tablets, pills, powders, lozenges, sachets, cachets, elixirs, suspensions, emulsions, solutions, syrups, soft and hard gelatin capsules, and other orally ingestible formulations.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include lubricating agents such as talc, magnesium stearate, and mineral oil; wetting agents; emulsifying and suspending agents; preserving agents such as methyl- and propyl-hydroxybenzoates, sweetening agents; and flavoring agents. The compositions of the present invention can also be formulated so as to provide quick, sustained or delayed release of Ace or Ace analog after administration to the patient by employing procedures known in the art.

Pharmaceutical compositions with Ace or Ace analogs may have other compounds added which may aid in the administration and/or adsorption and/or uptake of Ace or Ace analog. For example, combining Ace or Ace analog with calcium-dependent secretagogues may result in a higher level of chloride secretion. One such calcium-dependent secretagogue is carbachol.

While the invention has been described in detail and with reference to specific embodiments thereof, it will be apparent to one of ordinary skill in the art that various changes and modifications can be made therein without departing from the spirit and scope thereof. The artisan will further acknowledge that the examples recited herein are demonstrative only and are not meant to be limiting.

I, the inventor, claim:

1. A method for treating a disease characterized by a defect in ion transport, wherein said disease is selected from the group consisting of cystic fibrosis, Dent's disease, X-linked nephrolithiasis, X-linked recessive hypophosphatemic rickets, autosomal dominant myotonia congenita, and autosomal recessive general myotonia, wherein said method comprises administering a therapeutically effective amount of a polypeptide consisting of the amino acid sequence of SEQ ID NO:5, to an animal having said disease, and wherein said method results in an increase in the amount of airway surface water in the lungs of said animal.

2. The method of claim 1, wherein said disease is cystic fibrosis.

3. The method of claim 1, wherein said therapeutically effective amount of said polypeptide is the amount of said polypeptide administered which results in between 0.2 μg and 500μg of said polypeptide per $cm^2$ of bronchial surface area.

4. The method of claim 3, wherein said therapeutically effective amount of said polypeptide is the amount of said polypeptide administered which results in between 0.5μg and 10μg of said polypeptide per $cm^2$ of bronchial surface area.

5. The method of claim 1, wherein said animal has reduced ciliary activity in the lungs of said animal, and said method results in an increase in ciliary activity in the lungs of said animal.

6. The method of claim 1, wherein said animal has reduced ciliary activity in the lungs of said animal, and said method results in an increase in ciliary activity in the lungs of said animal, wherein said reduced ciliary activity results from a decrease in the amount of chloride being secreted from bronchial epithelial cells in said animal.

7. The method of claims 5, or 6, wherein the therapeutically effective amount of said polypeptide is the amount of said polypeptide administered which results in between 0.2μg and 500μg of said polypeptide per $cm^2$ of bronchial surface area.

8. The method of claims 7, wherein the therapeutically effective amount of said polypeptide is the amount of said polypeptide administered which results in between 0.5μg and 10μg of said polypeptide per $cm^2$ of bronchial surface area.

9. The method of claim 1, wherein said animal has reduced chloride secretion from bronchial epithelial cells in the lungs of said animal, and said method results in an increase in chloride secretion from bronchial epithelial cells in the lungs of said animal.

* * * * *

SEQUENCE LISTING

```
<160> NUMBER OF SEQ ID NOS: 19

<210> SEQ ID NO 1
<211> LENGTH: 291
<212> TYPE: DNA
<213> ORGANISM: Vibrio cholerae
<300> PUBLICATION INFORMATION:
<308> DATABASE ACCESSION NUMBER: Genbank/ Z22569
<309> DATABASE ENTRY DATE: 1995-05-12

<400> SEQUENCE: 1
atgcttatga tggacaccct ttatgactgg ctaattgatg gctttacgtg gcttgtgatc      60
aagctcggta ttatgtggat tgagagcaag atttttgtta tccaattctt ctgggagatg     120
tcccagaaag tgattgatat gtttaccatc tatccgctta tccaacaggc tatcgatatg     180
ctgcctcctc aatacagcgg ctttctgttc tttttagggt tagaccaagc gctggctatc     240
gtgcttcagg ctttgatgac ccgttttgcc ctgcgagcgt taaacctat

Val Ile Gln Phe Phe Trp Glu Met Ser Gln Lys Val Ile Asp Met Phe
            35                  40                  45

Thr Ile Tyr Pro Leu Ile Gln Gln Ala Ile Asp Met Leu Pro Pro Gln
        50                  55                  60

Tyr Ser Gly Phe Leu Phe Phe Leu Gly Leu Asp Gln Ala Leu Ala Ile
65                  70                  75                  80

Val Leu Gln Ala Leu Met Thr Arg Phe Ala Leu Arg Ala Leu Asn Leu
                85                  90                  95

<210> SEQ ID NO 3
<211> LENGTH: 73
<212> TYPE: PRT
<213> ORGANISM: Artificial Sequence
<220> FEATURE:
<223> OTHER INFORMATION: Ace analog. Mutated Ace polypeptide truncated
      at amino acid 73.

<400> SEQUENCE: 3

Met Leu Met Met Asp Thr Leu Tyr Asp Trp Leu Ile Asp Gly Phe Thr
1               5                   10                  15

Trp Leu Val Ile Lys Leu Gly Ile Met Trp Ile Glu Ser Lys Ile Phe
            20                  25                  30

Val Ile Gln Phe Phe Trp Glu Met Ser Gln Lys Val Ile Asp Met Phe
            35                  40                  45

Thr Ile Tyr Pro Leu Ile Gln Gln Ala Ile Asp Met Leu Pro Pro Gln
        50                  55                  60

Tyr Ser Gly Phe Leu Phe Phe Leu Gly
65                  70

<210> SEQ ID NO 4
<211> LENGTH: 57
<212> TYPE: PRT
<213> ORGANISM: Artificial Sequence
<220> FEATURE:
<223> OTHER INFORMATION: Ace analog. Mutated Ace polypeptide truncated
      at amino acid 57.

<400> SEQUENCE: 4

Met Leu Met Met Asp Thr Leu Tyr Asp Trp Leu Ile Asp Gly Phe Thr
1               5                   10                  15

Trp Leu Val Ile Lys Leu Gly Ile Met Trp Ile Glu Ser Lys Ile Phe
            20                  25                  30

Val Ile Gln Phe Phe Trp Glu Met Ser Gln Lys Val Ile Asp Met Phe
            35                  40                  45

Thr Ile Tyr Pro Leu Ile Gln Gln Ala
        50                  55

<210> SEQ ID NO 5
<211> LENGTH: 42
<212> TYPE: PRT
<213> ORGANISM: Artificial Sequence
<220> FEATURE:
<223> OTHER INFORMATION: Ace analog. Mutated Ace polypeptide truncated
      at amino acid 42.

<400> SEQUENCE: 5

Met Leu Met Met Asp Thr Leu Tyr Asp Trp Leu Ile Asp Gly Phe Thr
1               5                   10                  15

Trp Leu Val Ile Lys Leu Gly Ile Met Trp Ile Glu Ser Lys Ile Phe
            20                  25                  30

```
Val Ile Gln Phe Phe Trp Glu Met Ser Gln
        35                  40
```

<210> SEQ ID NO 6
<211> LENGTH: 34
<212> TYPE: PRT
<213> ORGANISM: Artificial Sequence
<220> FEATURE:
<223> OTHER INFORMATION: Ace analog.  Mutated Ace polypeptide truncated
                        at amino acid 34.

<400> SEQUENCE: 6

```
Met Leu Met Met Asp Thr Leu Tyr Asp Trp Leu Ile Asp Gly Phe Thr
1               5                   10                  15

Trp Leu Val Ile Lys Leu Gly Ile Met Trp Ile Glu Ser Lys Ile Phe
            20                  25                  30

Val Ile
```

<210> SEQ ID NO 7
<211> LENGTH: 96
<212> TYPE: PRT
<213> ORGANISM: Artificial Sequence
<220> FEATURE:
<223> OTHER INFORMATION: Ace analog.  Mutated Ace polypeptide with
                        substitution of lysine at position 43 to
                        alanine.

<400> SEQUENCE: 7

```
Met Leu Met Met Asp Thr Leu Tyr Asp Trp Leu Ile Asp Gly Phe Thr
1               5                   10                  15

Trp Leu Val Ile Lys Leu Gly Ile Met Trp Ile Glu Ser Lys Ile Phe
            20                  25                  30

Val Ile Gln Phe Phe Trp Glu Met Ser Gln Ala Val Ile Asp Met Phe
        35                  40                  45

Thr Ile Tyr Pro Leu Ile Gln Gln Ala Ile Asp Met Leu Pro Pro Gln
    50                  55                  60

Tyr Ser Gly Phe Leu Phe Phe Leu Gly Leu Asp Gln Ala Leu Ala Ile
65                  70                  75                  80

Val Leu Gln Ala Leu Met Thr Arg Phe Ala Leu Arg Ala Leu Asn Leu
                85                  90                  95
```

<210> SEQ ID NO 8
<211> LENGTH: 96
<212> TYPE: PRT
<213> ORGANISM: Artificial Sequence
<220> FEATURE:
<223> OTHER INFORMATION: Ace analog.  Mutated Ace polypeptide with
                        substitution of lysine at position 21 to
                        alanine.

<400> SEQUENCE: 8

```
Met Leu Met Met Asp Thr Leu Tyr Asp Trp Leu Ile Asp Gly Phe Thr
1               5                   10                  15

Trp Leu Val Ile Ala Leu Gly Ile Met Trp Ile Glu Ser Lys Ile Phe
            20                  25                  30

Val Ile Gln Phe Phe Trp Glu Met Ser Gln Lys Val Ile Asp Met Phe
        35                  40                  45

Thr Ile Tyr Pro Leu Ile Gln Gln Ala Ile Asp Met Leu Pro Pro Gln
    50                  55                  60

Tyr Ser Gly Phe Leu Phe Phe Leu Gly Leu Asp Gln Ala Leu Ala Ile
65                  70                  75                  80
```

```
Val Leu Gln Ala Leu Met Thr Arg Phe Ala Leu Arg Ala Leu Asn Leu
                85                  90                  95

<210> SEQ ID NO 9
<211> LENGTH: 96
<212> TYPE: PRT
<213> ORGANISM: Artificial Sequence
<220> FEATURE:
<223> OTHER INFORMATION: Ace analog.  Mutated Ace polypeptide with
                        substitution of lysine at position 30 to
                        alanine.

<400> SEQUENCE: 9

Met Leu Met Met Asp Thr Leu Tyr Asp Trp Leu Ile Asp Gly Phe Thr
1               5                   10                  15

Trp Leu Val Ile Lys Leu Gly Ile Met Trp Ile Glu Ser Ala Ile Phe
            20                  25                  30

Val Ile Gln Phe Phe Trp Glu Met Ser Gln Lys Val Ile Asp Met Phe
        35                  40                  45

Thr Ile Tyr Pro Leu Ile Gln Gln Ala Ile Asp Met Leu Pro Pro Gln
    50                  55                  60

Tyr Ser Gly Phe Leu Phe Phe Leu Gly Leu Asp Gln Ala Leu Ala Ile
65                  70                  75                  80

Val Leu Gln Ala Leu Met Thr Arg Phe Ala Leu Arg Ala Leu Asn Leu
                85                  90                  95

<210> SEQ ID NO 10
<211> LENGTH: 96
<212> TYPE: PRT
<213> ORGANISM: Artificial Sequence
<220> FEATURE:
<223> OTHER INFORMATION: Ace analog.  Mutated Ace polypeptide with
                        substitution of glutamic acid at position 28 to
                        alanine.

<400> SEQUENCE: 10

Met Leu Met Met Asp Thr Leu Tyr Asp Trp Leu Ile Asp Gly Phe Thr
1               5                   10                  15

Trp Leu Val Ile Lys Leu Gly Ile Met Trp Ile Ala Ser Lys Ile Phe
            20                  25                  30

Val Ile Gln Phe Phe Trp Glu Met Ser Gln Lys Val Ile Asp Met Phe
        35                  40                  45

Thr Ile Tyr Pro Leu Ile Gln Gln Ala Ile Asp Met Leu Pro Pro Gln
    50                  55                  60

Tyr Ser Gly Phe Leu Phe Phe Leu Gly Leu Asp Gln Ala Leu Ala Ile
65                  70                  75                  80

Val Leu Gln Ala Leu Met Thr Arg Phe Ala Leu Arg Ala Leu Asn Leu
                85                  90                  95

<210> SEQ ID NO 11
<211> LENGTH: 96
<212> TYPE: PRT
<213> ORGANISM: Artificial Sequence
<220> FEATURE:
<223> OTHER INFORMATION: Ace analog.  Mutated Ace polypeptide with
                        substitution of glutamic acid at position 39 to
                        alanine.

<400> SEQUENCE: 11

Met Leu Met Met Asp Thr Leu Tyr Asp Trp Leu Ile Asp Gly Phe Thr
1               5                   10                  15

Trp Leu Val Ile Lys Leu Gly Ile Met Trp Ile Glu Ser Lys Ile Phe
```

20                  25                  30
Val Ile Gln Phe Phe Trp Ala Met Ser Gln Lys Val Ile Asp Met Phe
            35                  40                  45

Thr Ile Tyr Pro Leu Ile Gln Gln Ala Ile Asp Met Leu Pro Pro Gln
        50                  55                  60

Tyr Ser Gly Phe Leu Phe Phe Leu Gly Leu Asp Gln Ala Leu Ala Ile
65                  70                  75                  80

Val Leu Gln Ala Leu Met Thr Arg Phe Ala Leu Arg Ala Leu Asn Leu
                85                  90                  95

<210> SEQ ID NO 12
<211> LENGTH: 96
<212> TYPE: PRT
<213> ORGANISM: Artificial Sequence
<220> FEATURE:
<223> OTHER INFORMATION: Ace analog.  Mutated Ace polypeptide with
      substitution of methionine at position 1 to
      alanine.

<400> SEQUENCE: 12

Ala Leu Met Met Asp Thr Leu Tyr Asp Trp Leu Ile Asp Gly Phe Thr
1               5                   10                  15

Trp Leu Val Ile Lys Leu Gly Ile Met Trp Ile Glu Ser Lys Ile Phe
            20                  25                  30

Val Ile Gln Phe Phe Trp Glu Met Ser Gln Lys Val Ile Asp Met Phe
        35                  40                  45

Thr Ile Tyr Pro Leu Ile Gln Gln Ala Ile Asp Met Leu Pro Pro Gln
    50                  55                  60

Tyr Ser Gly Phe Leu Phe Phe Leu Gly Leu Asp Gln Ala Leu Ala Ile
65                  70                  75                  80

Val Leu Gln Ala Leu Met Thr Arg Phe Ala Leu Arg Ala Leu Asn Leu
                85                  90                  95

<210> SEQ ID NO 13
<211> LENGTH: 96
<212> TYPE: PRT
<213> ORGANISM: Artificial Sequence
<220> FEATURE:
<223> OTHER INFORMATION: Ace analog.  Mutated Ace polypeptide with
      substitution of methionine at position 3 to
      alanine.

<400> SEQUENCE: 13

Met Leu Ala Met Asp Thr Leu Tyr Asp Trp Leu Ile Asp Gly Phe Thr
1               5                   10                  15

Trp Leu Val Ile Lys Leu Gly Ile Met Trp Ile Glu Ser Lys Ile Phe
            20                  25                  30

Val Ile Gln Phe Phe Trp Glu Met Ser Gln Lys Val Ile Asp Met Phe
        35                  40                  45

Thr Ile Tyr Pro Leu Ile Gln Gln Ala Ile Asp Met Leu Pro Pro Gln
    50                  55                  60

Tyr Ser Gly Phe Leu Phe Phe Leu Gly Leu Asp Gln Ala Leu Ala Ile
65                  70                  75                  80

Val Leu Gln Ala Leu Met Thr Arg Phe Ala Leu Arg Ala Leu Asn Leu
                85                  90                  95

<210> SEQ ID NO 14
<211> LENGTH: 96
<212> TYPE: PRT
<213> ORGANISM: Artificial Sequence

```
<220> FEATURE:
<223> OTHER INFORMATION: Ace analog.  Mutated Ace polypeptide with
                         substitution of methionine at position 4 to
                         alanine.

<400> SEQUENCE: 14

Met Leu Met Ala Asp Thr Leu Tyr Asp Trp Leu Ile Asp Gly Phe Thr
1               5                   10                  15

Trp Leu Val Ile Lys Leu Gly Ile Met Trp Ile Glu Ser Lys Ile Phe
            20                  25                  30

Val Ile Gln Phe Phe Trp Glu Met Ser Gln Lys Val Ile Asp Met Phe
        35                  40                  45

Thr Ile Tyr Pro Leu Ile Gln Gln Ala Ile Asp Met Leu Pro Pro Gln
    50                  55                  60

Tyr Ser Gly Phe Leu Phe Leu Gly Leu Asp Gln Ala Leu Ala Ile
65                  70                  75                  80

Val Leu Gln Ala Leu Met Thr Arg Phe Ala Leu Arg Ala Leu Asn Leu
                85                  90                  95

<210> SEQ ID NO 15
<211> LENGTH: 91
<212> TYPE: PRT
<213> ORGANISM: Artificial Sequence
<220> FEATURE:
<223> OTHER INFORMATION: Ace analog.  Mutated Ace polypeptide with
                         deletion of five aminoacids starting at
                         position 41.

<400> SEQUENCE: 15

Met Leu Met Met Asp Thr Leu Tyr Asp Trp Leu Ile Asp Gly Phe Thr
1               5                   10                  15

Trp Leu Val Ile Lys Leu Gly Ile Met Trp Ile Glu Ser Lys Ile Phe
            20                  25                  30

Val Ile Gln Phe Phe Trp Glu Met Asp Met Phe Thr Ile Tyr Pro Leu
        35                  40                  45

Ile Gln Gln Ala Ile Asp Met Leu Pro Pro Gln Tyr Ser Gly Phe Leu
    50                  55                  60

Phe Phe Leu Gly Leu Asp Gln Ala Leu Ala Ile Val Leu Gln Ala Leu
65                  70                  75                  80

Met Thr Arg Phe Ala Leu Arg Ala Leu Asn Leu
                85                  90

<210> SEQ ID NO 16
<211> LENGTH: 85
<212> TYPE: PRT
<213> ORGANISM: Artificial Sequence
<220> FEATURE:
<223> OTHER INFORMATION: Ace analog.  Mutated Ace polypeptide with
                         deletion of eleven amino acids starting at
                         position 35.

<400> SEQUENCE: 16

Met Leu Met Met Asp Thr Leu Tyr Asp Trp Leu Ile Asp Gly Phe Thr
1               5                   10                  15

Trp Leu Val Ile Lys Leu Gly Ile Met Trp Ile Glu Ser Lys Ile Phe
            20                  25                  30

Val Ile Asp Met Phe Thr Ile Tyr Pro Leu Ile Gln Gln Ala Ile Asp
        35                  40                  45

Met Leu Pro Pro Gln Tyr Ser Gly Phe Leu Phe Phe Leu Gly Leu Asp
    50                  55                  60
```

```
Gln Ala Leu Ala Ile Val Leu Gln Ala Leu Met Thr Arg Phe Ala Leu
 65                  70                  75                  80

Arg Ala Leu Asn Leu
                 85

<210> SEQ ID NO 17
<211> LENGTH: 42
<212> TYPE: PRT
<213> ORGANISM: Artificial Sequence
<220> FEATURE:
<223> OTHER INFORMATION: Ace analog.  Mutated Ace polypeptide with
                        truncation at amino acid position 42 and
                        substitution of lysine at position 21 to
                        alanine.

<400> SEQUENCE: 17

Met Leu Met Met Asp Thr Leu Tyr Asp Trp Leu Ile Asp Gly Phe Thr
 1               5                  10                  15

Trp Leu Val Ile Ala Leu Gly Ile Met Trp Ile Glu Ser Lys Ile Phe
                20                  25                  30

Val Ile Gln Phe Phe Trp Glu Met Ser Gln
         35                  40

<210> SEQ ID NO 18
<211> LENGTH: 42
<212> TYPE: PRT
<213> ORGANISM: Artificial Sequence
<220> FEATURE:
<223> OTHER INFORMATION: Ace analog.  Mutated Ace polypeptide with
                        truncation at amino acid position 42 and
                        substitution of glutamic acid at position 28 to
                        alanine.

<400> SEQUENCE: 18

Met Leu Met Met Asp Thr Leu Tyr Asp Trp Leu Ile Asp Gly Phe Thr
 1               5                  10                  15

Trp Leu Val Ile Lys Leu Gly Ile Met Trp Ile Ala Ser Lys Ile Phe
                20                  25                  30

Val Ile Gln Phe Phe Trp Glu Met Ser Gln
         35                  40

<210> SEQ ID NO 19
<211> LENGTH: 42
<212> TYPE: PRT
<213> ORGANISM: Artificial Sequence
<220> FEATURE:
<223> OTHER INFORMATION: Ace analog.  Mutated Ace polypeptide with
                        truncation at amino acid position 42 and
                        substitution of lysine at position 21 to
                        alanine and of glutamic acid at position 28 to
                        alanine.

<400> SEQUENCE: 19

Met Leu Met Met Asp Thr Leu Tyr Asp Trp Leu Ile Asp Gly Phe Thr
 1               5                  10                  15

Trp Leu Val Ile Ala Leu Gly Ile Met Trp Ile Ala Ser Lys Ile Phe
                20                  25                  30

Val Ile Gln Phe Phe Trp Glu Met Ser Gln
         35                  40
```